(12) United States Patent
Wöhrle et al.

(10) Patent No.: US 7,708,559 B2
(45) Date of Patent: *May 4, 2010

(54) DENTAL IMPLANT SYSTEM

(75) Inventors: Peter S. Wöhrle, Corona Del Mar, CA (US); Charles W. Howlett, Laguna Beach, CA (US)

(73) Assignee: Nobel Biocare Services AG, Glattbrugg (CH)

(*) Notice: Subject to any disclaimer, the term of this patent is extended or adjusted under 35 U.S.C. 154(b) by 746 days.

This patent is subject to a terminal disclaimer.

(21) Appl. No.: 10/846,351

(22) Filed: May 14, 2004

(65) Prior Publication Data

US 2005/0014108 A1 Jan. 20, 2005

Related U.S. Application Data

(60) Provisional application No. 60/471,036, filed on May 16, 2003, provisional application No. 60/472,234, filed on May 21, 2003, provisional application No. 60/479,530, filed on Jun. 18, 2003.

(51) Int. Cl.
*A61C 8/00* (2006.01)
(52) U.S. Cl. ..................................................... 433/174
(58) Field of Classification Search ................. 433/172, 433/173, 174, 175, 176, 223, 169
See application file for complete search history.

(56) References Cited

U.S. PATENT DOCUMENTS

| | | | |
|---|---|---|---|
| 2,112,007 A | 3/1938 | Adams | |
| 3,849,887 A | 11/1974 | Brainin | |
| 4,051,598 A | 10/1977 | Sneer | |
| 4,416,629 A | 11/1983 | Mozsary et al. | |

(Continued)

FOREIGN PATENT DOCUMENTS

CH 413224 5/1966

(Continued)

OTHER PUBLICATIONS

Strub et al., "The Re Implant® System for Immediate Implant Placement". Journal of Esthetic Dentistry 1997, vol. 9, pp. 187-196.

(Continued)

*Primary Examiner*—Ralph A Lewis
(74) *Attorney, Agent, or Firm*—Knobbe, Martens, Olson & Bear, LLP.

(57) ABSTRACT

A dental implant assembly for supporting a dental prosthesis. The assembly comprises a dental implant and an abutment. The dental implant comprises a body portion, a collar portion and a central bore. The body portion is located at a distal end of the dental implant and is configured to lie at least substantially below a crest of a patient's jawbone. The collar portion is located at a proximal end of the dental implant and forms an abutment mating surface which defines an outer edge that has a generally scalloped shape. The central bore extends through the collar portion and into the implant body portion. The central bore includes a threaded portion and a post portion. The abutment comprises a post configured to fit within the post portion of the central bore and an implant mating surface that is configured to mate with the abutment mating surface of the dental implant.

13 Claims, 20 Drawing Sheets

U.S. PATENT DOCUMENTS

| | | | |
|---|---|---|---|
| 4,468,200 A | 8/1984 | Münch | |
| 4,624,673 A | 11/1986 | Meyer | |
| 4,713,003 A | 12/1987 | Symington et al. | |
| 4,812,120 A | 3/1989 | Flanagan et al. | |
| 4,856,994 A | 8/1989 | Lazzara et al. | |
| 4,960,381 A | 10/1990 | Niznick | |
| 5,004,422 A | 4/1991 | Propper | |
| 5,035,619 A | 7/1991 | Daftary | |
| 5,049,074 A | 9/1991 | Otani et al. | |
| 5,125,839 A * | 6/1992 | Ingber et al. | 433/169 |
| 5,246,370 A | 9/1993 | Coatoam | |
| 5,282,746 A | 2/1994 | Sellers et al. | |
| 5,282,747 A | 2/1994 | Nordin | |
| 5,310,343 A | 5/1994 | Hasegawa et al. | |
| 5,328,371 A | 7/1994 | Hund et al. | |
| 5,417,568 A | 5/1995 | Giglio | |
| 5,417,569 A | 5/1995 | Perisse | |
| 5,431,567 A | 7/1995 | Daftary | |
| 5,458,488 A * | 10/1995 | Chalifoux | 433/173 |
| 5,464,440 A | 11/1995 | Joahansson | |
| 5,527,182 A | 6/1996 | Willoughby | |
| 5,584,693 A | 12/1996 | Nishihara | |
| 5,588,838 A | 12/1996 | Hansson et al. | |
| 5,622,500 A | 4/1997 | Niznick | |
| 5,636,989 A | 6/1997 | Somborac et al. | |
| 5,667,384 A * | 9/1997 | Sutter et al. | 433/172 |
| 5,674,069 A | 10/1997 | Osorio | |
| 5,695,334 A * | 12/1997 | Blacklock et al. | 433/173 |
| 5,759,034 A | 6/1998 | Daftary | |
| 5,779,480 A | 7/1998 | Groll et al. | |
| 5,876,454 A | 3/1999 | Nanci et al. | |
| 5,908,298 A | 6/1999 | Dürr et al. | |
| 5,931,675 A | 8/1999 | Callan | |
| 5,989,027 A | 11/1999 | Wagner et al. | |
| 5,989,029 A | 11/1999 | Osorio et al. | |
| 6,012,923 A * | 1/2000 | Bassett et al. | 433/172 |
| 6,024,567 A | 2/2000 | Callan | |
| 6,142,782 A | 11/2000 | Lazarof | |
| 6,162,054 A | 12/2000 | Takacs | |
| 6,164,969 A | 12/2000 | Dinkelacker | |
| 6,174,167 B1 | 1/2001 | Wöhrle | |
| 6,217,331 B1 | 4/2001 | Rogers et al. | |
| 6,217,333 B1 | 4/2001 | Ercoli | |
| 6,227,858 B1 | 5/2001 | Lundgren | |
| 6,231,342 B1 | 5/2001 | Osorio et al. | |
| 6,273,720 B1 | 8/2001 | Spalten | |
| 6,280,195 B1 | 8/2001 | Broberg et al. | |
| 6,283,753 B1 * | 9/2001 | Willoughby | 433/172 |
| 6,283,754 B1 | 9/2001 | Wöhrle | |
| 6,287,115 B1 | 9/2001 | Lustig et al. | |
| 6,312,260 B1 | 11/2001 | Kumar et al. | |
| 6,350,126 B1 | 2/2002 | Levisman | |
| 6,364,663 B1 | 4/2002 | Dinkelacker | |
| 6,431,867 B1 | 8/2002 | Gittelson et al. | |
| 6,464,500 B1 | 10/2002 | Popovic | |
| 6,527,554 B2 | 3/2003 | Hurson et al. | |
| 6,619,958 B2 | 9/2003 | Beaty et al. | |
| 6,626,911 B1 | 9/2003 | Engman et al. | |
| 6,652,765 B1 | 11/2003 | Beaty | |
| 6,854,972 B1 * | 2/2005 | Elian | 433/173 |
| 6,939,135 B2 * | 9/2005 | Sapian | 433/174 |
| 2001/0021498 A1 | 9/2001 | Osorio et al. | |
| 2002/0182567 A1 * | 12/2002 | Hurson et al. | 433/173 |
| 2003/0031981 A1 * | 2/2003 | Holt | 433/173 |
| 2003/0031982 A1 | 2/2003 | Abarno | |
| 2003/0068599 A1 | 4/2003 | Balfour et al. | |
| 2003/0124489 A1 | 7/2003 | Hurson et al. | |
| 2005/0014108 A1 | 1/2005 | Wohrle et al. | |
| 2005/0214714 A1 | 9/2005 | Wohrle | |
| 2006/0188846 A1 | 8/2006 | Wohrle et al. | |
| 2006/0194170 A1 | 8/2006 | Wohrle et al. | |
| 2006/0246398 A1 | 11/2006 | Groll et al. | |

FOREIGN PATENT DOCUMENTS

| | | |
|---|---|---|
| DE | 250 052 A1 | 9/1954 |
| DE | 43 39 060 A1 | 9/1993 |
| EP | 0 705 574 | 4/1996 |
| EP | 0 820 737 | 1/1998 |
| EP | 0 868 889 A1 | 10/1998 |
| EP | 1 013 236 | 12/1998 |
| FR | 2 317 904 | 2/1977 |
| GB | 1291470 | 10/1972 |
| IT | 540713 | 3/1956 |
| JP | 08-117250 | 5/1996 |
| JP | 10-033562 | 2/1998 |
| WO | WO 96/29020 | 9/1996 |
| WO | WO 97/37610 | 10/1997 |
| WO | WO 98/42273 | 10/1998 |
| WO | WO 00/32134 | 6/2000 |
| WO | WO 01/49199 A2 | 7/2001 |
| WO | WO 01/49199 A3 | 7/2001 |
| WO | WO 01/50972 A2 | 7/2001 |
| WO | WO 03/000909 | 11/2003 |
| WO | WO 03/059189 | 11/2003 |

OTHER PUBLICATIONS

Kohal et al., "Custom-made root analogue titanium implants placed into extraction sockets". Clinical Oral Implants Research 1997, vol. 8, pp. 386-392.

Heydecke et al., "Optimal Esthetics in Single Tooth Replacement with the Re-implant System: A Case Report". The International Journal of Prosthodontics 1999, vol. 12, pp. 184-189.

Baier, et al., "Future Directions in Surface Preparation of Dental Implants", Journal of Dental Education, 52:788-791.

Bengazi, et al., 1996, "Recession of the soft tissue margin at oral implants", Clinical Oral Implants Research, 7:303-310.

Branemark, et al., 1985, "Tissue-Integrated Prosthesis: Nature and Significance of the Edentulous State" Quintessence Publishing Co., Inc., chapter 2:77-88.

Brunski, John B., 1988, Biomechanics of Oral Implants: Future Research Directions, Journal of Dental Education, 52:775-787.

Buser, et al., 1991, "Tissue Integration of One-Stage ITI Implants: 3 year Results of a Longitudinal Study With Hollow-Cylinder and Hollow-Screw Implants.", The International Journal of Oral & Maxillofacial Implants, 6:405-412.

Buser, et al., 1996m "Comparison of healed tissues adjacent to submerged and non-submerged unloaded titanium dental implants", Clinical Oral Implants Research, 7:11-19.

Chiche, et al., 1998, "Multidisplinary Implant Dentistry for improved Aesthetics and Function", Pract Periodont. Aesthet. Dent., 10:177-186.

Gieloff et al., 1995, Bio-Design-Implantate Sofortimplantate mit dem Re implant System, p. 252-256 (with English translation).

Gomez-Roman, et al., 1997, "The Frialit-2 Implant System: Five-Year Clinical Experience in Single-Tooth and Immediately Postextraction Applications", The International Journal of Oral & Maxillofacial Implant, 12:299-309.

Jansen, et al., 1997, "Microbial Leakage and Marginal Fit of the Implant-Abutment Interface", The International Journal of Oral & Maxillofacial Implants, 12:527-540.

Kirsch, et al., 1989., "The IMZ Osteointegrated Implant System", Dental Clinics of North America, 33:733-791.

Kohal et al., 1996., "Wurzelanagoge Titanimplantate (Bio-Design-Implantate) für die Sofortimplatnation-Das Re-Implant® -System", p. 99-115 (with English Translation).

Krauser, Jack T., 1989., "Hydorxylapatite-Coated Dental Implants", Dental Clinics of North America, 33:879-903.

Langer, et al., 1993, "The Wide Fixture: A Solution for special Bone Situations and a Rescue for the Compromised Implant. Part 1", the International Journal of Oral & Maxillofacial Implants, 8:400-408.

Meffert, Roland M., DDS, 1988, "The Soft Tissue Interface in Dental Implantology", Journal of Dental Education, 52:810-878.

Niznick, Gerald A., Oct. 1989, "A Multimodal Approach to Implant Prosthodontics", Dental Clinics of North America, 33:869-878.

Olsson, et al., 1995, "MkII-A Modified Self-Tapping Branemark Implant: 3-Year Results of a Controlled Prospective Pilot Study", The International Journal of Oral & Maxillofacial Implant, 10:15-21.

Prestipino, et al., Jan./Feb. 1993, "esthetic High-Strength Implant Abutments. Part 1", Journal of Esthetic Dentistry, p. 29-35.

W. Eugene Roberts, DDS, Ph.D., 1998, "Bone Tissue Interface", Journal of Dental Education, 52:804-809.

Saadoun, et al., 1998, "Peridontal Implications in Implant Treatment Planning of Aesthtic Results", Pract. Periodont. Asthet. Dent., 10:655-664.

Schnitman, et al., 1988, Implants for Partial Edentulism, Journal of Dental Education, 52:725-736.

Siegele, et al., 1989, "Numerical Investigations of the Influence of Implant Shape on Stress Distribution in the Jaw Bone", the International Journal of Oral & maxillofacial Implants, 4:333-340.

Sullivan, et al., May/Jun. 1993, "Considerations for Successful Single tooth Implant Restorations", Journal of Esthetic Dentistry, 5:119-124.

Wennerberg, et al., "Design and Surface Characteristics of 13 Commercially Available Oral Implant Systems", International Journal of Oral & Maxillofacial Implants, 8:622-633.

F.A. Young, D.Sc., 1988, "Future Directions in Dental Implants Materials Research", Journal of Dental Education 52:770-774.

International Search Report for Application No. PCT/US2006/002471 (the PCT counterpart of the parent application).

U.S. Appl. No. 11/406,626, filed Apr. 19, 2006, titled Dental Implant System.

U.S. Appl. No. 11/406,782, filed Apr. 19, 2006, titled Dental Implant System.

Reissue U.S. Appl. No. 10/366,531 of U.S. Patent No. 6,283,754, filed Feb. 12, 2003.

Reexamination U.S. Appl. No. 90/007,836 of U.S. Patent No. 6,283,754, filed on Dec. 2, 2005.

U.S. Appl. No. 11/043,683, filed Jan. 26, 2005, titled Dental Implant System.

* cited by examiner

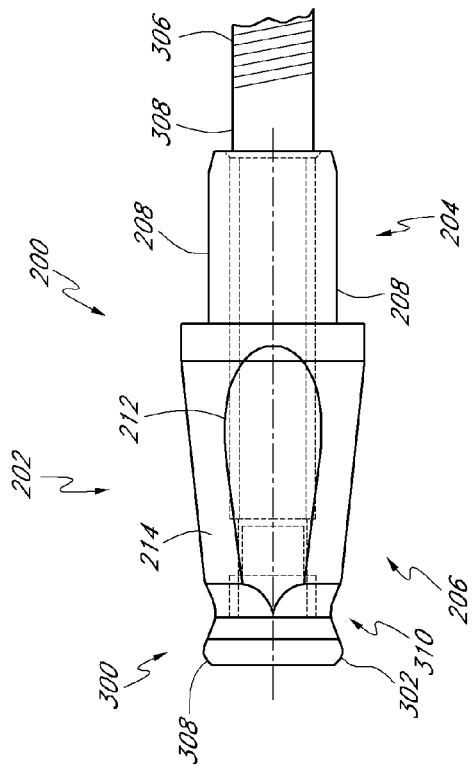
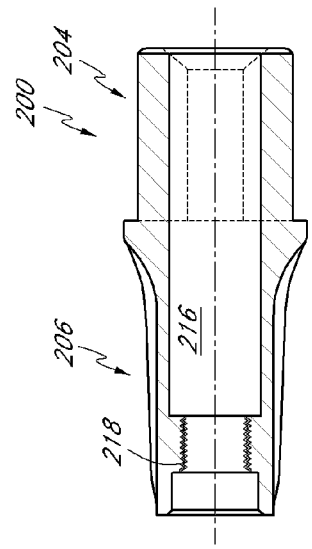
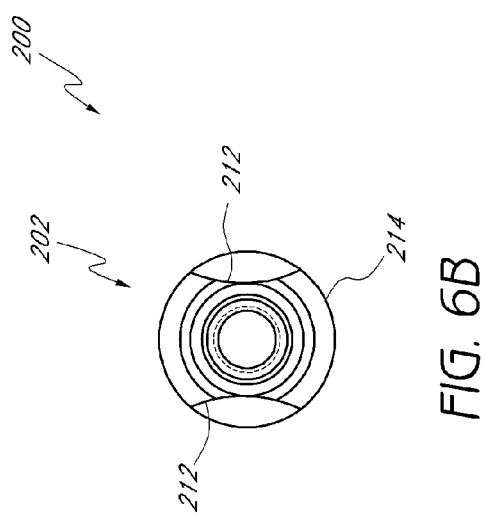
FIG. 6A
FIG. 6C
FIG. 6B

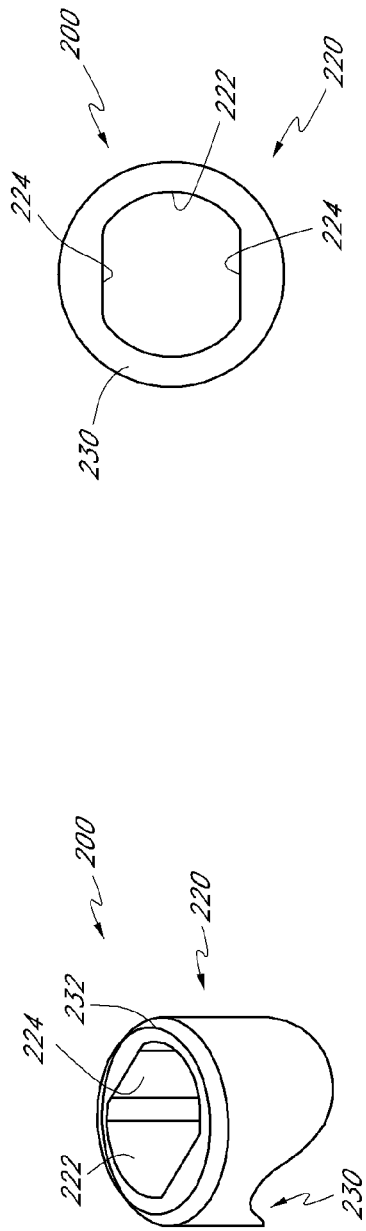
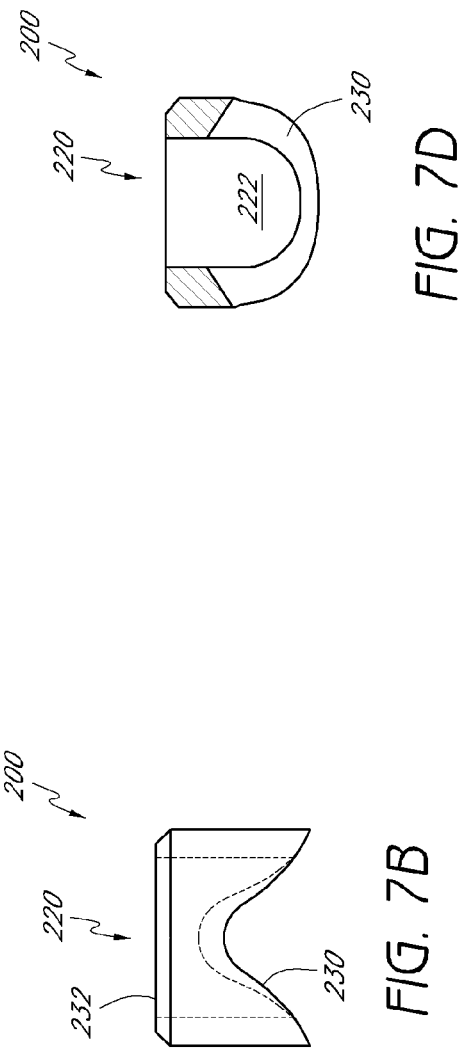
FIG. 7C
FIG. 7D
FIG. 7A
FIG. 7B

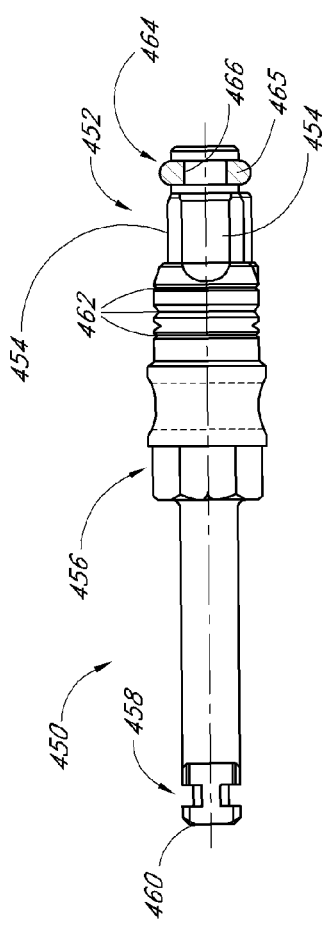
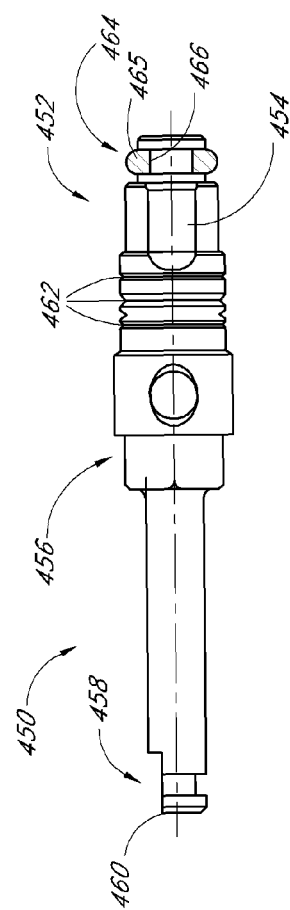
FIG. 10A
FIG. 10B

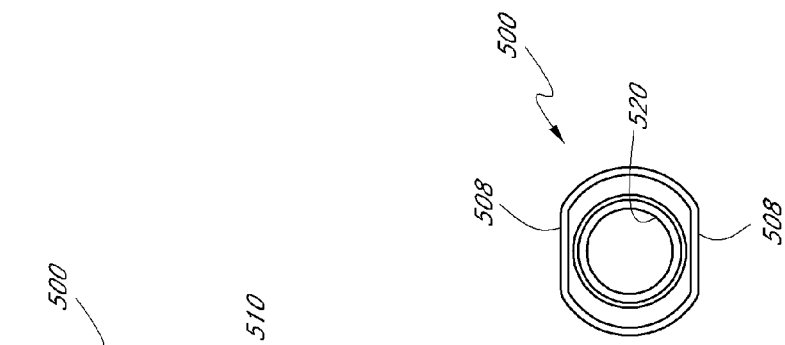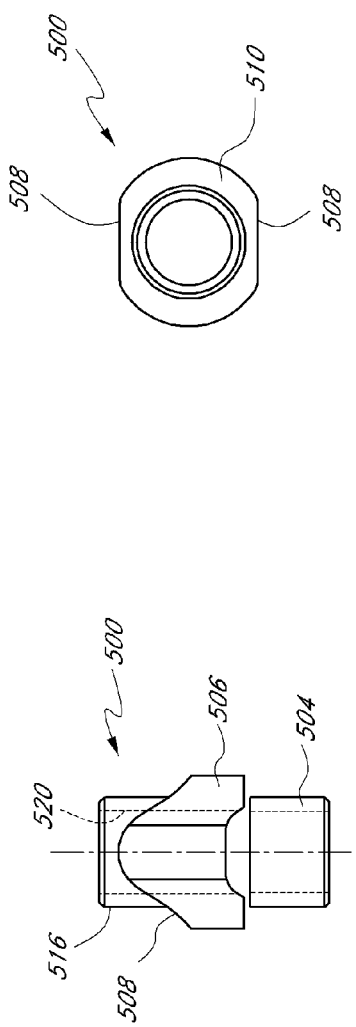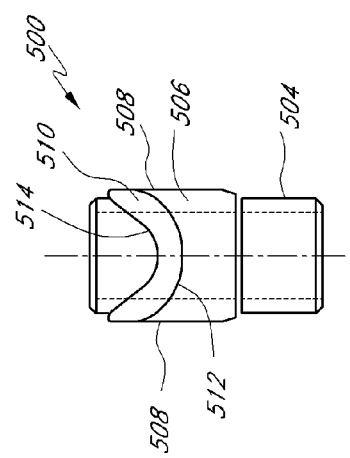

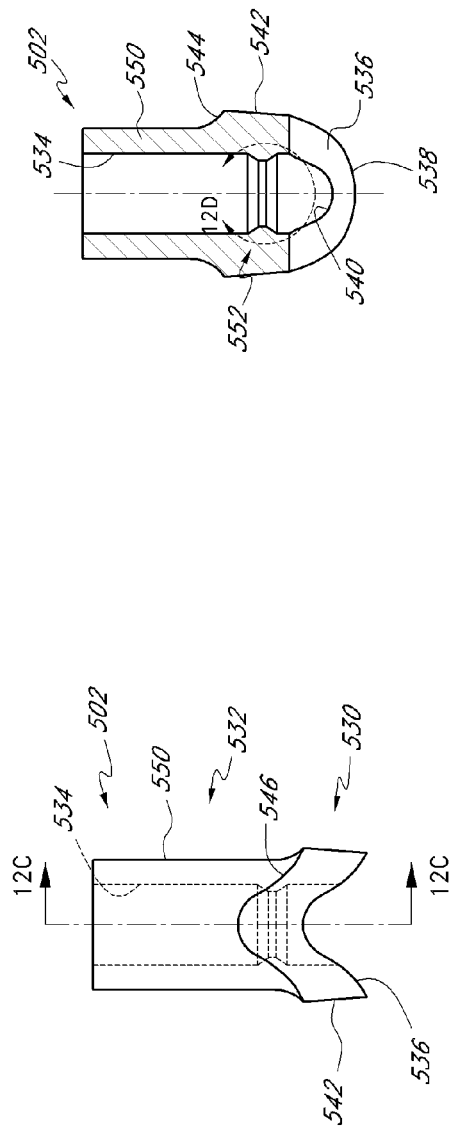
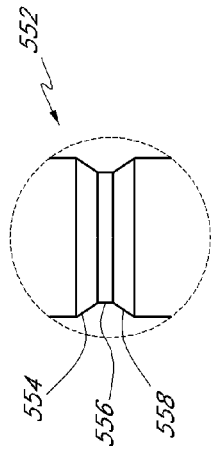
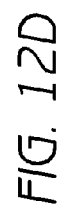
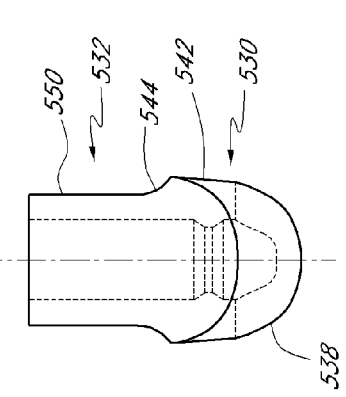

DENTAL IMPLANT SYSTEM

PRIORITY INFORMATION

This application claims the priority benefit under 35 U.S.C. §119(e) of Provisional Application 60/471,036 filed May 16, 2003 entitled "Dental Implant System", Provisional Application 60/472,234 filed May 21, 2003, and Provisional Application 60/479,530 filed Jun. 18, 2003, the entirety all of these applications are hereby incorporated by reference herein.

BACKGROUND OF THE INVENTION

1. Field of the Invention

The present invention relates generally to dental implants and, more particularly, to an improved dental implant system.

2. Description of the Related Art

Implant dentistry involves the restoration of one or more teeth in a patient's mouth using artificial components. Such artificial components typically include a dental implant and a prosthetic tooth and/or a final abutment that is secured to the dental implant. Generally, the process for restoring a tooth is carried out in three stages.

Stage I involves implanting the dental implant into the alveolar bone (i.e., jawbone) of a patient. The surgeon first accesses the alveolar bone through the patient's gum tissue and removes any remains of the tooth to be replaced. Next, the specific site in the alveolar bone where the implant will be anchored is preparing by drilling and/or reaming to accommodate the width of the dental implant to be inserted. Then, the dental implant is inserted into the hole, typically by screwing, although other techniques are known for introducing the implant in the jawbone.

After the implant is initially installed in the bone, a temporary healing cap is secured over the exposed proximal end in order to seal an internal bore of the implant. The patient's gums are then sutured over the implant to allow the implant site to heal and to allow desired osseointegration to occur. Complete osseointegration typically takes anywhere from three to ten months.

During stage II, the surgeon reaccesses the implant fixture by making an incision through the patient's gum tissues. The healing cap is then removed, exposing the proximal end of the implant. Typically, an impression coping in attached to the implant and a mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site. In a modified procedure, an abutment or other transmucosal component is either integrally formed with the implant or attached to the implant during stage I. In such a procedure, stages I and II are effectively combined in to a single stage.

Stage III involves fabricating and placement of a cosmetic tooth prosthesis to the implant fixture. The plaster analogue provides laboratory technicians with a model of the patient's mouth, including the orientation of the implant fixture and/or abutment relative to the surrounding teeth. Based on this model, the technician constructs a final restoration. The final step in the restorative process is replacing the temporary healing abutment with the final abutment and attaching a final prosethesis to the final abutment.

The dental implant is typically fabricated from pure titanium or a titanium alloy. The dental implant typically includes a body portion and a collar. The body portion is configured to extend into and osseointegrate with the alveolar bone. The top surface of the collar typically lies flush with the crest of the jawbone bone. The final abutment typically lies on the top surface and extends through the soft tissue, which lies above the alveolar bone. As mentioned above, the abutment supports the final prostheses. Typically, the coronal or crown portion of the collar and the portions of the final abutment that extend through the soft tissue have a machined or polished surfaces. This arrangement is believed in the art to prevent the accumulation of plaque and calculus and facilitates cleaning.

SUMMARY OF THE INVENTION

One embodiment of the present inventions comprises the recognition that the body's natural defense mechanisms tend to provide approximately a 1-3 millimeter zone of soft tissue between the abutment-implant interface (i.e., microgap) and the alveolar crest. This zone is referred to as the "biological width" and is present around natural teeth as well as dental implants. The biological width typically extends 360 degrees around the implant and lies coronal to the alveolar crest and apical to the prosthetic crown margin (approximately 2.5-3 millimeters). The biological width consists of approximately 1 millimeter gingival sulcus, 1 millimeter epithelial attachment and 1 millimeter connective tissue zone. In prior art implants, the abutment-implant interface typically lies flush with the alveolar crest. As such, the bone tissue is reabsorbed and the alveolar crest retreats until the proper biological width can be reestablished. This bone loss is undesirable both aesthetically and structurally.

Another embodiment of the invention is the recognition that in the prior art typically provides for a flat interface (i.e., microgap) between the abutment and the collar of the implant. However, due to the irregular configuration of the alveolar crest, a flat interface makes it difficult to conform to a proper biological width in all 360 degrees around the implant. A proper biological width that does not extend for all 360 degrees around the implant can produce undesirable bone loss.

Another embodiment of the invention is the recognition that in the prior art dental implants typically include a bone apposition surface with a top surface that is generally flat. Due to the height discrepancy between the buccal and approximal aspect of the osteotomy, portions of the bone may lie above the bone apposition surface. This may result in bone loss, which is undesirable especially in esthetically demanding areas such as the anterior maxilla.

One embodiment of the present invention comprises a dental implant assembly for supporting a dental prosthesis. The assembly comprises a dental implant having a body portion located at a distal end of the dental implant. The body portion is configured to lie at least substantially below a crest of a patient's jawbone. A collar portion is located at a proximal end of the dental implant. The collar portion forms a mating surface which defines an outer edge that has at least one peak and valley to match the contours of a patient's soft tissue. A central bore extends through the collar portion and into the implant body portion. The central bore including an engagement portion and a post portion. A post includes an upper portion, a lower portion and an inner bore extending through the upper and lower portions. The lower portion is configured to fit at least partially within the post portion of the implant. The post has at least one elastic portion. A ceramic abutment having a central bore and a lower mating surface that is configured to mate with the mating surface of the dental implant. A coupling member is configured to extend through the central bore of the abutment and the inner bore of the post and to engage the engagement portion of the implant. When the coupling member is tightened, the centering post seals the interface between the ceramic abutment and the implant to inhibit material from entering the central bore of the implant.

Another embodiment of the invention comprises an abutment and sealing post combination for supporting a dental prosthesis on a dental implant. The abutment has a central bore, an upper portion a lower portion. The lower portion forms a mating surface which defines an outer edge that has at least one peak and valley to match the contours of a patient's soft tissue. An elastic post includes an upper portion, a lower portion and an inner bore extending through the upper and lower portions. The lower portion is configured to fit within a dental implant. The upper portion forms a shoulder that follows the contours of the mating surface of the implant.

Another embodiment of the invention comprise an impression pin for recording the orientation of a dental implant. The impression pin comprises a lower portion comprising a mating surface which defines an outer edge that has at least one peak and valley to match the contours of a patient's soft tissue. An upper portion is configured to engage impression material of an impression tray.

Another embodiment of the invention comprises a method for installing a dental prosthesis. The methods includes providing a dental implant comprising a body portion located at a distal end of the dental implant, the body portion configured to lie at least substantially below a crest of a patient's jawbone, a collar portion located at a proximal end of the dental implant, the collar portion forming a mating surface which defines an outer edge that has at least one peak and valley to match the contours of a patient's soft tissue; a central bore that extends through the collar portion and into the implant body portion, the central bore including a threaded portion and a post portion. A post is provided that includes an upper portion, a lower portion and an inner bore extending through the upper and lower portions, the lower portion being configured to fit at least partially within the post portion of the implant, the post having at least one elastic portion. A ceramic abutment is provided. The ceramic abutment having a central bore and a lower mating surface that is configured to mate with the mating surface of the dental implant. A coupling member is configured to extend through the central bore of the abutment and the inner bore of the post and to engage the engagement portion of the implant. The dental implant is inserted into a bone. The post is inserted into the central bore of the implant. The ceramic abutment is positioned onto the implant and over the post. The ceramic abutment is secured to the dental implant by tightening the coupling member and compressing the post to form a tight seal between the ceramic abutment and the implant.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of this invention will now be described with reference to the drawings of a preferred embodiment which is intended to illustrate and not to limit the invention. The drawings contain the following figures:

FIG. 6A is a side view of an exemplary embodiment of a first portion of an impression coping and a coupling bolt having certain features and advantages according to the present invention;

FIG. 6B is a top view of the first portion of the impression coping of FIG. 6A;

FIG. 6C is a cross-sectional view of the first portion of the impression coping of FIG. 6A;

FIG. 7A is a side perspective view of a second portion of an impression coping having certain features and advantages according to the present invention;

FIG. 7B is a front view of an exemplary embodiment of a first portion of the impression coping of FIG. 7A;

FIG. 7C is a cross-sectional side view of the impression coping of FIG. 7A; and

FIG. 7D is a bottom view of the impression coping of FIG. 7A;

FIG. 10A is a side view of an insertion tool;

FIG. 10B is another side view of the insertion tool of FIG. 10A;

FIG. 11A is a side view of a centering post having certain features and advantages according to the present invention;

FIG. 11B is a front view of the centering post of FIG. 11A;

FIG. 11C is a top view of the centering post of FIG. 11A;

FIG. 11D is a bottom view of the centering post of FIG. 11A.

FIG. 12A is a side view of an abutment having certain features and advantages according to the present invention;

FIG. 12B is a front view of the abutment of FIG. 12A;

FIG. 12C is a cross-sectional view taken through line 12C-12C of FIG. 12A;

FIG. 12D is a closer view of a portion of FIG. 12C

DETAILED DESCRIPTION OF THE PREFERRED EMBODIMENTS

Figure 1A:
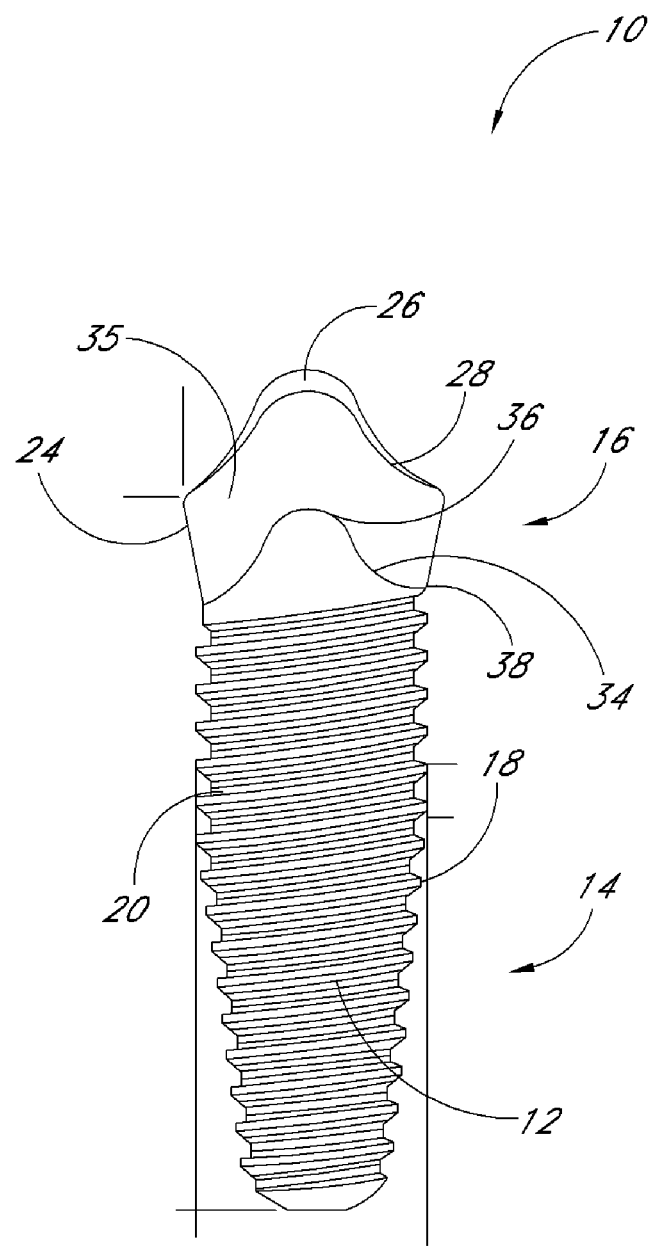
FIG. 1A is a side view of an exemplary embodiment of a dental implant having certain features and aspects of the present invention.

FIGS. 1A-D illustrate an exemplary embodiment of a dental implant 10. In this embodiment, the implant 10 comprises an implant body 12, which preferably includes a lower portion 14 and a collar 16. The implant 10 may be made of titanium although other materials may also be used. The lower portion 14 is preferably tapered and includes threads 18 that match preformed threads made along the inner surface of a bore in the patient's jawbone (not shown). However, it should be appreciated that the lower portion 14 can be configured so as to be self-tapping or unthreaded. It should also bee appreciated that although the illustrated lower portion 14 is tapered or conical it may also be substantially cylindrical.

In the illustrated embodiment, the lower portion 14 preferably has a bone apposition surface 20, which is configured to promote osseointegration. In one embodiment, the bone apposition surface 20 increases the surface area of the lower portion 12. For example, the bone apposition surface 20 can be formed by roughening the lower portion 12 in several different manners, such as, for example, acid-etching (e.g., to apply an oxidized titanium surface to such as the oxidized surface manufactured by Nobel Biocare under the trademark TiUnite™), grit blasting, and/or machining. Alternatively, the bone apposition surface 20 can be formed by coating the lower surface with a substance that increases the surface area of the lower portion 12. Calcium phosphate ceramics, such as tricalcium phosphate (TCP) and hydroxyapatite (HA) are examples of suitable materials. In other embodiments, the bone apposition surface 20 may comprise macroscopic structures, such as, for example, threads, micro-threads, indentations, grooves that are configured to promote osseointegration and may be used alone or combined with the roughening and/or the coatings described above.

Figure 1C:
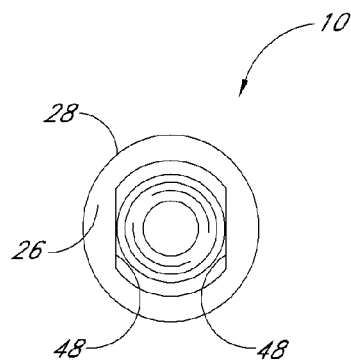
FIG. 1C is a top view of the dental implant of FIG. 1A.
Figure 1D:
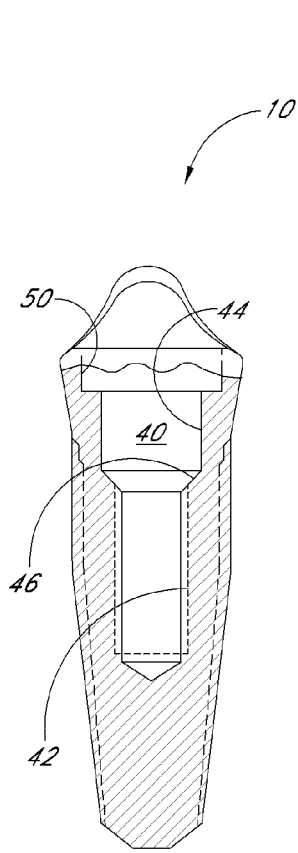
FIG. 1D is a cross-sectional view of the dental implant of FIG. 1A taken along line 1D-1D.
Figure 1B:
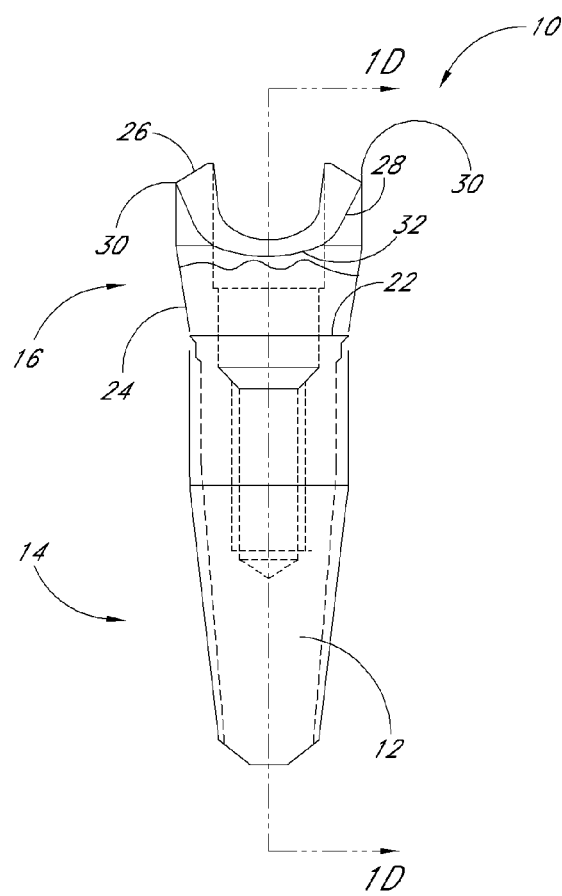
FIG. 1B is a front view of the dental implant of FIG. 1A shown without threads.

The collar 16 lies above (i.e., proximal) the lower portion 12 and in the illustrated embodiment is integrally formed with or permanently affixed to the lower portion 12 at a collar/implant interface 22 (see FIG. 1B). The collar 16 is defined in part by a side wall 24. In the illustrated embodiment, the side wall 24 is tapered with respect to the longitudinal axis of the implant 10 at an angle of approximately 30 degrees. However, in modified embodiments, the side wall 24 can be cylindrical or substantially cylindrical. The illustrated collar 16 also has a substantially circular cross-section (see FIG. 1C). However, in modified embodiments, the collar 16 may have a non-round cross-section.

As best seen in FIGS. 1A-C, the collar 16 includes a top surface 26. As will be described in more detail below, the top surface 26 may support a final restoration. In the illustrated embodiment, an outer edge 28 of the top surface 26 has a curved or scalloped shape with at least one and more preferably two peaks 30 and valleys 32 that follow or at least closely approximate the shape of the naturally occurring contours of a patient's soft-tissue morphology.

In one embodiment, the outer edge 28 is configured so as to be positioned at approximately the same height as the top surfaces of the naturally occurring soft-tissue morphology. In such embodiments, the peaks 30 of the outer edge 28 lie approximately 2-5 millimeters above the collar/body interface 22 while the valleys 32 lie approximately 1-5 millimeters below the peaks 30. In one embodiment, the peak 30 lies approximately 4 millimeters above the collar body interface 25 and the valleys 32 lie approximately 2 millimeters below the peak. Although not illustrated it should be appreciated that in modified embodiments the peaks and valleys may have different heights. That is, the two peaks may have different heights as compared to each other. In a similar manner, the two valleys may have different heights as compared to each other.

As best seen in FIG. 1B, in the illustrated embodiment, the top surface 26 is beveled with respect to a line that is perpendicular longitudinal axis of the implant 10. In one preferred embodiment, the top surface 26 beveled at an angle of 30 degrees. In modified embodiments, the top surface 26 may be perpendicular to the longitudinal axis (i.e., flat) or beveled at other angles. However, the illustrated embodiment advantageously provides a particularly solid foundation for the final restoration.

With reference to FIG. 1A, a top edge 34 of the bone tissue apposition surface 20 preferably extends above the collar/implant interface 22 and onto the collar 16. As with the outer edge 28, the top edge 34 preferably has a curved or scalloped shape with at least one and more preferably two peaks 36 and valleys 38 that follow or at least closely approximate the shape of the naturally occurring contours of a patient's bone-tissue morphology. In the illustrated embodiment, the peaks 36 and valleys 38 of the top edge 34 are aligned with the peaks 30 and valleys 32 of the outer edge 34. Although not illustrated, it should be appreciated that in other embodiments the threads 18 may extend up to the top edge 34 or at least partially up the collar 16 below the top edge 34. It should also be appreciated that in other embodiments, the peaks 36 and valleys 38 may be approximated by various combinations of straight and/or curved lines that follow or at least closely approximate the shape of the naturally occurring contours of a patient's bone-tissue morphology.

In the illustrated arrangement, the valleys 38 of the top edge 34 lie slightly above or at the collar/implant interface the peak 30. The peaks 36 may lie approximately 1-5 millimeters above the valleys. In one embodiment, the peaks 36 lie approximately 2 millimeters above the valleys 38. As with the outer edge 28, it should be appreciated that in modified embodiments the peaks 36 and valleys 38 may have different heights. That is, the two peaks 36 may have different heights as compared to each other. In a similar manner, the two valleys 38 may have different heights as compared to each other.

The surface 35 of the collar 16 above the top edge may be polished to reduce accumulation of plaque and calculus. In a modified embodiment, the surface 35 may be treated to promote, enhance or maintain soft-tissue attachment. Such treatments may include applying growth factor, applying protein, roughening and/or the application of coatings that increase surface area. In addition, the surface 35 may be modified or covered with a coating that changes the color of the collar 16. For example, in one embodiment the surface 35 is coated with a material hydroxyapatite (HA) or other ceramic coatings that are generally white or "tooth-like" in color.

With reference to FIG. 1D, the exemplary implant 10 includes a central bore 40. In the illustrated embodiment, the central bore 40 includes a threaded section 42 for receiving a threaded portion of a bolt or screw (described below) and post-receiving section 44, which preferably includes a tapered portion 46 adjacent the threaded section 42. The post-receiving 44 section may include anti-rotational features, such as, for example, flat sides, grooves, and or indentations. In the illustrated arrangement, the anti-rotational feature comprises a pair of flat sides 48 (see FIG. 1C), which are positioned in an enlarged diameter portion 50 of the post-receiving section 44.

In one embodiment of use, the implant 10 is positioned in the bone such that the peaks 36 of the bone apposition surface 30 are positioned at approximately the same level as the interproximal bone adjacent the implant 10.

Figure 2B:
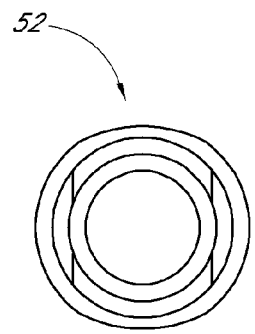
FIG. 2B is a top view of the abutment of FIG. 2A.
Figure 2A:
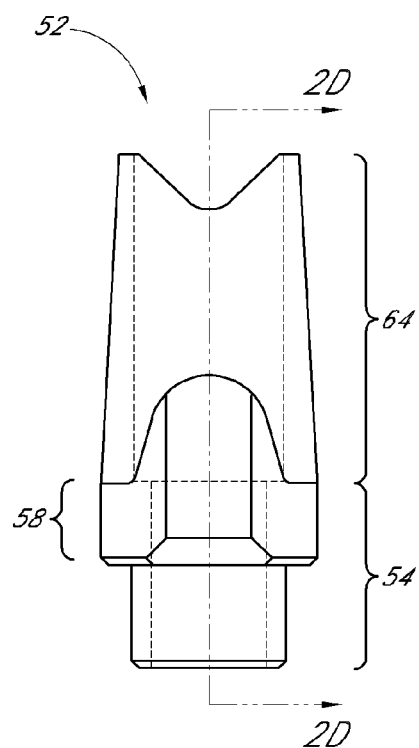
FIG. 2A is a side view of an exemplary embodiment of an abutment, which is configured to mate with the implant of FIG. 1A and has certain features and aspects of the present invention.

FIGS. 2A-D illustrate an abutment 52, which is configured to mate with the implant 10 described above. In the illustrated arrangement, the abutment 52 includes a lower portion 54 (see FIG. 2A) that is configured to fit within the post-receiving section 44 of the implant 10. As mentioned above, the post-receiving section 44 may include anti-rotational features. If the post-receiving section 46 includes such anti-rotational features, the lower portion 54 preferably includes corresponding structures so as to prevent the abutment 52 from rotating with respect to the implant body 10. Accordingly, the lower portion 54 of the illustrated embodiment includes a pair of flat sides 56 (FIG. 2C) on an enlarged diameter section 58 of the lower portion 54 (FIG. 2A).

Figure 2D:
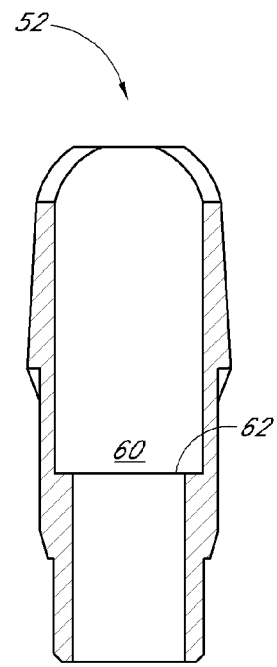
FIG. 2D is a cross-sectional view of the abutment of FIG. 2A taken along line 2D-2D.
Figure 2C:
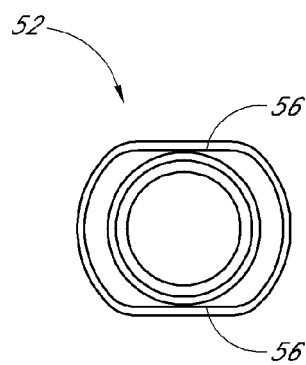
FIG. 2C is a bottom view of the abutment of FIG. 2A.

As best seen in FIG. 2D, the abutment 52 preferably includes a central through bore 60, which includes a shoulder 62. The central bore 60 and shoulder 62 are configured to receive a bolt and example of which is illustrated in FIGS. 3A and 3B.

Figure 3B:
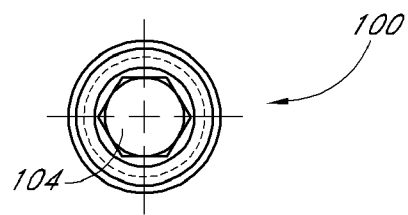
FIG. 3B is a top view of the coupling bolt of FIG. 3A.
Figure 3A:
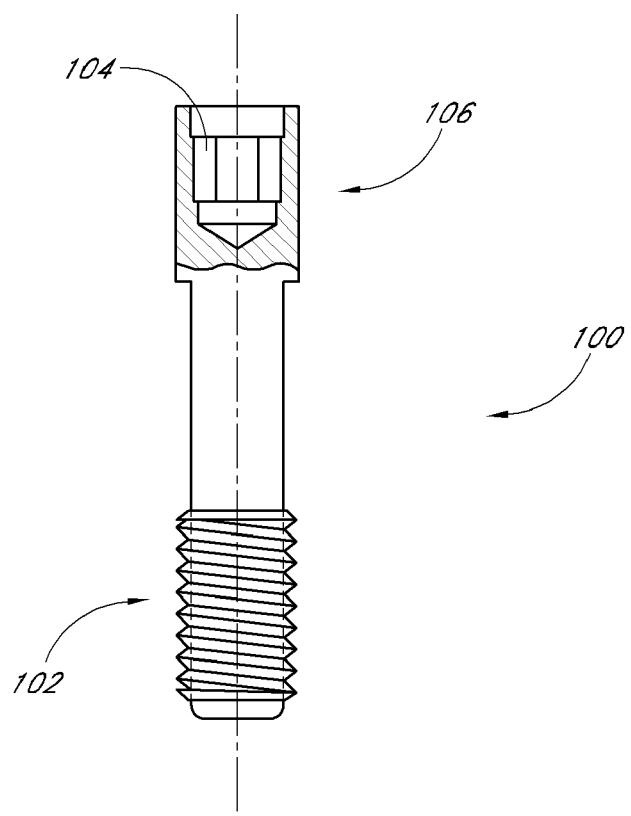
FIG. 3A is a side view of an exemplary embodiment of a coupling bolt having certain features and aspects according to the present invention.
Figure 3C:
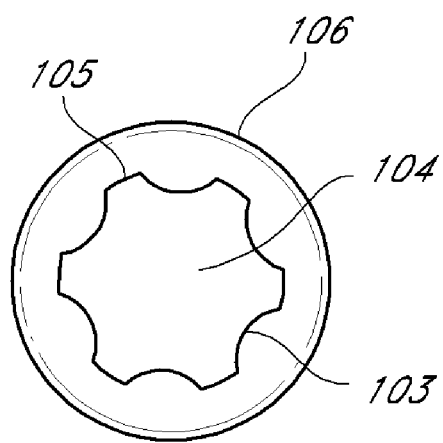
FIG. 3C is a top view of another embodiment of a coupling bolt.

Turning now to FIGS. 3A and 3B, the coupling screw 100 is sized and dimensioned to extend through the bore 60 and to couple the abutment 52 to the implant 10. The coupling screw 100 has an externally threaded lower region 102. The threaded lower region 102 is sized and dimensioned to engage the threads of the threaded chamber 42 of the implant 10. The illustrated coupling screw 102 includes a hexagonal recess 104 located within a head 106 of the screw 100. The hexagonal recess 104 allows for the insertion of a hexagonally shaped tool such as a conventional Allen® wrench, which can be used to apply rotational force to the coupling screw 100. Of course, the head 106 of the screw 100 may include any of a variety of other rotational engagement connections. For example, in one embodiment (see FIG. 3C, the head 106 includes a tapered recess 104' comprising plurality of concave side portions 103 interconnected by flat or slightly curved side portions (see also the internal connection marketed under the trademark Unigrip™ by Nobel Biocare AB).

Figure 2E:
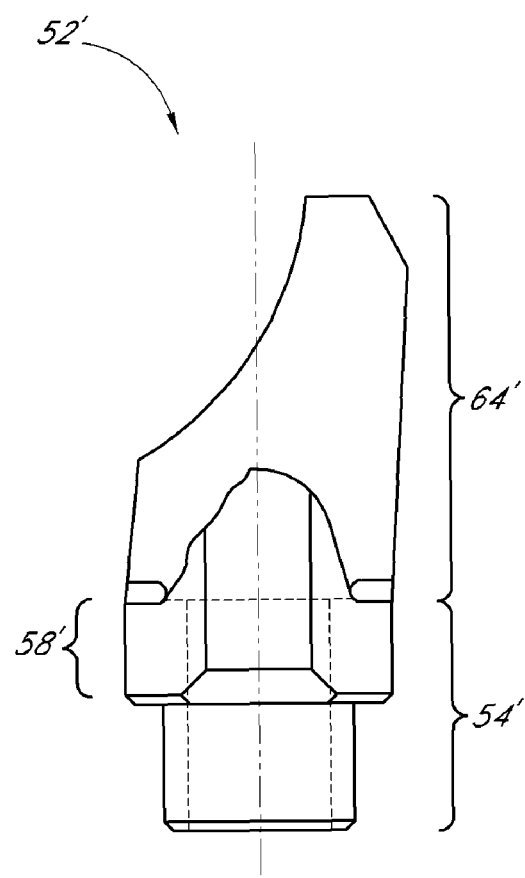
FIG. 2E is a side view of a modified embodiment of the abutment of FIG. 2A.

With reference back to FIG. 2A, the abutment has an upper portion 64, which, when the lower portion 54 is in the implant 10, is configured to lie above the top surface 26 of the implant 10. The upper portion 64 may be shaped in various ways for supporting various dental components such as, for example, a final restorations and/or other dental components. In the illustrated embodiment, the upper portion 64 has a generally cylindrical shape with a slight taper. In other embodiments, the upper portion may be angled 64 (e.g., approximately 10 degrees with respect to the longitudinal axis of the bore 40) as shown in another embodiment of an abutment 52', which is illustrated in FIG. 2E and wherein like numbers are used to refer to components similar to the previous embodiment.

Figure 4A:
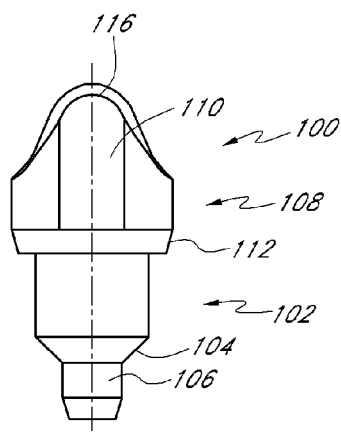
FIG. 4A is a side view of an exemplary embodiment of a healing plug having certain features and advantages according to the present invention.
Figure 4B:
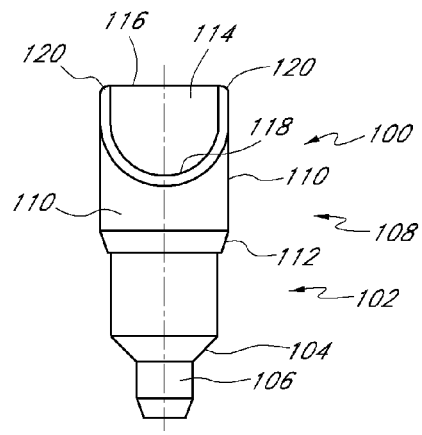
FIG. 4B is a front view of the healing plug of FIG. 5A.
Figure 4C:
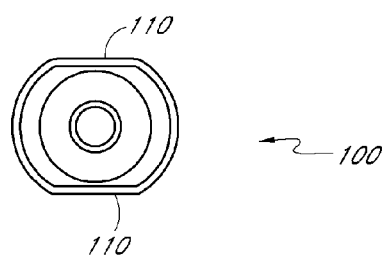
FIG. 4C is a top view of the healing plug of FIG. 5A.

FIGS. 4A-C illustrate an exemplary embodiment of a healing plug 100, which is also configured to mate with the implant 10 described above. The healing plug 100 may be used to cover the bore of the dental implant 10 so that patient's gums may be sutured over the dental implant 10 during a healing period, such as, for example, after stage one surgery. In this manner, the healing plug 100 may be used to prevent blood, body tissue and/or bacteria from entering the bore 40.

The healing cap 100 includes a first post 102 that is configured to fit within the post-receiving section 44 of the dental implant 10. As such, in the illustrated embodiment, the first post 102 includes a beveled portion 104 that is configured to seat against the tapered portion 46 of the post-receiving section 44. A second post 106 lies below the first post 106. The second post 106 is configured to fit within and to extend into the threaded section 42 of the inner bore 40. As shown in FIGS. 4A and 4B, in the illustrated embodiment, the end of the second post 106 may be beveled.

The healing plug 100 has an upper portion 108, which includes a side wall 181 that is configured to fit within the enlarged diameter portion 50 of the post receiving section 44. In the illustrated embodiment, the enlarged diameter portion 52 includes anti-rotational features 48. As such, the illustrated upper portion 108 also includes corresponding anti-rotational features 110, which are in the form of a pair of flat sides. As mentioned above, in modified embodiments, the anti-rotational features 48 of the implant may be in other forms or not provided and, as such, the healing plug 100 may be formed with modified anti-rotational features or without corresponding anti-rotational features. In the illustrated embodiment, the upper portion 108 includes a beveled lower portion 112 adjacent the first post 102. However, it should be appreciated that in modified embodiments the healing plug 100 may be formed with out this beveled portion 112 or the beveled portions described above.

The upper portion 108 also includes a top or upper surface 114 that is advantageously configured such that, when the healing cap 100 is fitted within the bore 40, the top or upper surface mates 114 with the top surface 26 of the implant 10 to substantially cover the bore 40 and to prevent material from entering the bore 40. In the illustrated embodiment, the upper surface 114 is also advantageously configured to sit approximately even with or flush with the top surface 26 of the implant 10 so as to generally not increase the overall height of the healing cap 114 and dental implant 10 combination. As such, in the illustrated embodiment, the upper portion 108 and the first post 102 are sized and dimensioned such that the upper surface 114 lies approximately flush with or even with the top surface 26. In addition, the upper surface 114 includes upper edges 116, which are configured to generally lie flush with and extend between the peaks 30 of the inner edge of the top surface 26. The upper surface 114 also includes a pair of lower edges 118, which are configured to lie approximately flush with the valleys 32 of the inner edge of the top surface 26. The portions of the upper surface 114 between the upper and lower edges 116, 118 are preferably configured so as to form a generally smooth profile with the top surface 26 of the implant 10. The upper surface 114 preferably also includes a beveled edge 120, which also helps to form a generally smooth profile with the top surface 26 of the implant 10. Although not illustrated, it should be appreciated that in modified embodiments the upper surface 114 of the plug 100 may be configured to have different shapes and/or to lie partially or wholly above and/or below the top surface 26 of the implant 10.

The healing plug 100 may be secured to the implant in a variety of manners. In one embodiment, the healing plug 100 may be sized and dimensioned so as to be form a friction fit with the bore 40 of the implant 10. In other embodiments, the healing plug 100 may be made from a elastic material that may deform slightly when inserted into the bore 40 so as to produce an generally outwardly directed force, which may enhance the friction fit. In either of these embodiments, water or another lubricant may be used to initially insert the healing plug 100 into the implant 10. In other embodiments, the healing plug 100 and the implant 10 may include any of a variety of corresponding structures (e.g., grooves, ridges, etc.) to produce an interference fit. For example, in one embodiment, the healing plug 100 may be configured to engage the threaded portion 42 of the implant 10. In still other embodiments, adhesives may used to secure the healing plug 100 to the implant 10. In one embodiment, a dental pick (not shown) may be inserted between the implant 10 and the healing plug 100 to pry the plug 100 from the implant 10. Although not illustrated, it should be appreciated that in modified embodiments, the healing plug 100 may be provided with an inner bore so that the healing plug 100 may be coupled to the implant 10 by a coupling screw.

The healing cap 174 may be made from any of a variety of materials. In one embodiment, the healing cap is made of a medical grade silicon material.

FIGS. 5A-D illustrate a healing abutment 150, which is also configured to mate with the implant 10 described above. The healing abutment 150 may be used to cover the dental implant 10 and shape the patient's gums during a healing period, such as, for example, after stage one and/or two surgery.

The healing abutment 150 includes a post 152 that is configured to fit within the post receiving section 44 of the dental implant 10. The healing abutment 150 preferably includes a central bore 154 with a shoulder 156. The central bore 154 and shoulder 156 are configured to receive a bolt or coupling screw such as the bolt described above. In this manner, the bolt can extend into the threaded section 42 to secure the healing abutment 150 to the dental implant 10.

The healing abutment 150 preferably includes a lower surface 158 (see FIG. 5D), which is configured to mate with the top surface 26 of the implant 10. As with the restoration, the top and lower surfaces 26, 82, are preferably configured such that, when the healing abutment 150 is secured to the implant 10 a smooth transition is formed between the outer surfaces of the implant 10 and the healing abutment 74. That is, the dimensions and contours of the outer edge 28 of the top surface 26 preferably closely match the dimensions and contours of an outer edge 160 of the lower surface 158 of the healing abutment 150. In modified embodiments, the lower surface 158 may extend below the top surface 26 of the implant 10 to promote tissue retraction.

Figure 5B:
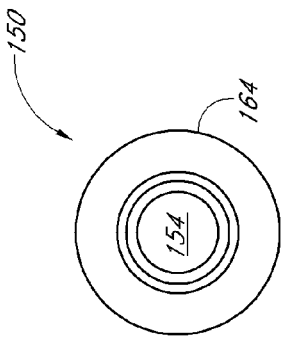
FIG. 5B is a top view of the healing cap of FIG. 5A.
Figure 5E:
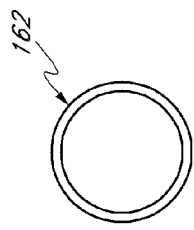
FIG. 5E is a side view of an exemplary embodiment of an O-ring that may be used with the healing cap of FIG. 5A and having certain features and advantages according to the present invention.
Figure 5C:
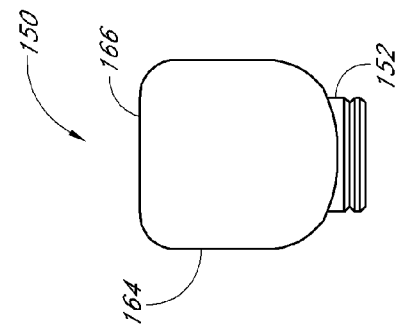
FIG. 5C is a front view of the healing cap of FIG. 5A.
Figure 5A:
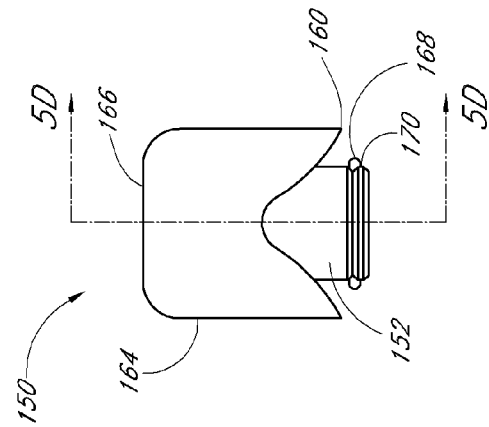
FIG. 5A is a side view of an exemplary embodiment of a healing cap having certain features and advantages according to the present invention.
Figure 5D:
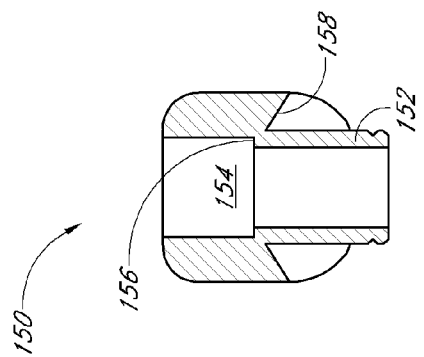
FIG. 5D is a cross-sectional view of the healing cap of FIG. 5A taken at line 5D-5D.
Figure 5G:
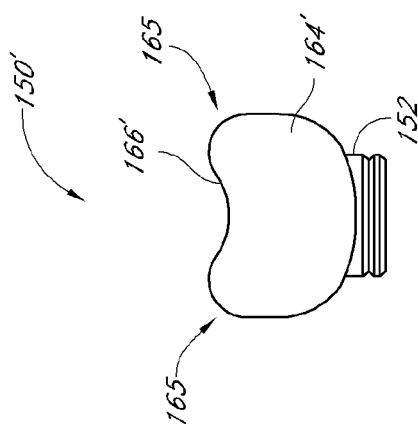
FIG. 5G is a front view of the healing cap of FIG. 5F.
Figure 5F:
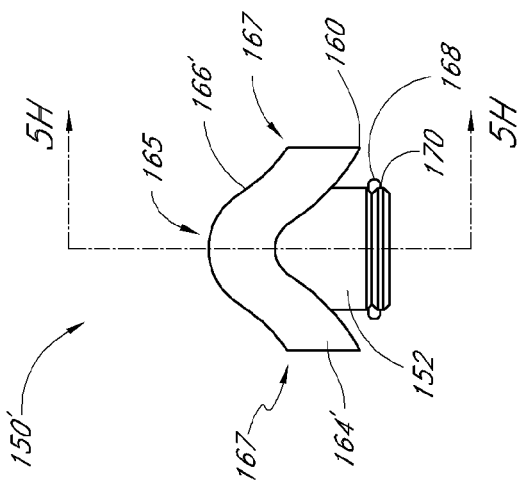
FIG. 5F is a side view of another exemplary embodiment of a healing cap having certain features ad advantages according to the present invention.
Figure 5H:
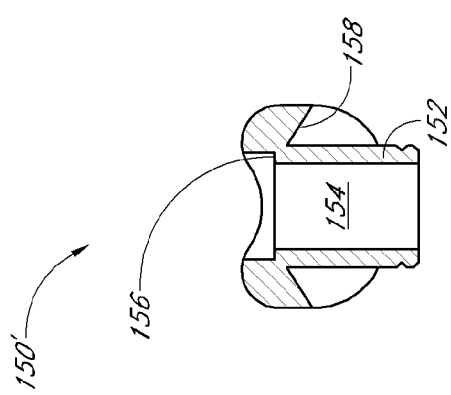
FIG. 5H is a cross-sectional view taken at line 5H-5H of FIG. 5F.

In one embodiment, an O-ring 162 (see FIG. 5E) may be placed between the lower surface 158 of the healing abutment 150 and the top surface 26 of the implant 10. The O-ring is compressed between the lower and top surfaces 158, 26 when the healing abutment 150 is secured to the implant 10 by a coupling screw to form a tight seal between the healing abutment 150 and the implant 10. It should be appreciated that an upper surface 164 of the healing abutment 150 may have a variety of shapes. For example, in the illustrated embodiment, the upper surface 164 of the healing abutment 165 is configured to shape the patient's gums during stage two surgery and has a generally cylindrical shape with a generally flat to surface 166. FIGS. 5E-G illustrate a modified embodiment of a healing abutment 150' with a modified upper surface 164'. In this embodiment, the upper surface 164' is advantageously configured such that it generally follows the contours of the lower surface 158 and the top surface 26 of the implant 10. As such, in the illustrated example, the upper surface 164' includes a top surface 166' that defines a pair peaks 165, which generally correspond to the peaks 30 of the implant 10, and a pair of valleys 167, which generally correspond to the valleys 32 of the implant 10. The abutment 150' may be used with a bolt (not illustrated) that has a top surface that is advantageously configured to sit approximately even with or flush with the top surface 166' of the abutment 150'.

In the illustrated embodiment, the post 152 includes a releasable retention feature 168, which is configured to releaseably engage the central bore 40 of the dental implant 10. The post 152 may include a variety of releasable retention features, such as, for example, prongs or compressible material, for creating a releasable retention force between the dental implant 10 and the healing abutment 150. In the illustrated embodiment, the releasable retention feature 168 comprises a resilient O-ring (shown in cross-section in FIG. 5A) positioned within an annular ridge and recess 170. The O-ring 168 may be configured to engage the inner surfaces of the central bore in a friction or interference fit. In this manner, the dental practitioner may temporarily attached the healing abutment 150 to the implant 10. The practitioner can then use both hands to manipulate a bolt and a driving instrument to secure the healing cap 150 to the implant 10. Of course, modified embodiments may be formed without this feature.

FIGS. 6A-C and 7A-9D illustrate first and second portions of an impression coping 200, which may be used when taking an impression of the patient's mouth to record the axial position and/or orientation of the implant 10. With initial reference to FIGS. 6A-C, the first portion includes a pin 202, which has a post 204 and an upper portion 206. The post 206 is configured to fit within the enlarged diameter portion 50 of the implant 10. As such, in the illustrated embodiment, the post 204 includes anti-rotational features 208 (e.g., flat sides), which are configured to mate with the anti-rotational features 48 of the implant 10. Although not illustrated, in modified embodiments, the post 206 may be configured to extend into the post receiving section 44 or the threaded section 42.

The upper portion 206 is configured to lie above the top surface 26 of the implant 10 and thus will be embedded in the impression material when the impression is being taken. When used as a transfer coping in a closed tray application, the upper portion 206 may include any of a variety of indexing features and/or attachment features, which may to record the axial position of the pin 202 and the implant 10 in the impression tray. In the illustrated embodiment, the indexing features comprise a pair of concave indentations 212 formed on the side wall 214 of the pin 202. Of course, in modified embodiments, other types of indexing features may be used (e.g., flat sides, grooves, etc.). For open tray or transfer cap applications, the upper portion 206 may include various retention structures (e.g., projections, lips, grooves, etc.) to enhance the retention force between the impression material the pin 202.

The illustrated pin 202 is provided with an inner bore 216 for receiving a bolt 300, which may be used to attach the pin 202 to the implant 10 when the impression is being taken. The bolt 300 includes a head portion 302 and an elongated shaft 304 with a threaded end 306. The head 302 lies above the top surface of the upper portion 206 and includes an side wall 308. As seen in FIG. 6A, the side wall 308 combines with the side wall of the upper portion 302 to form an axial groove or indentation 310. This indentation 310 is advantageously recorded in the impression and can be used by the practitioner to indicate that the impression pin 202 is properly reinserted into the impression. However, it should be appreciated that in modified embodiments (e.g., for transfer cap applications), the pin 202 may be formed without the inner bore 216 and used without the bolt 300. Capture threads 218 are preferably provided for temporarily coupling the bolt to the pin 202.

FIGS. 7A-D illustrate the second portion 220 of the impression coping 200. The second portion 220 includes an inner bore 222 configured to fit around the post 208 of the pin 202. As such, the inner bore 222 includes corresponding anti-rotational structures 224, which correspond to the anti-rotational structures on the pin 202. When assembled, the second portion 220 lies generally below the upper surface 206 of the pin 202 and may be slipped onto the post 206 and retained by a friction force. However, in modified embodiments, the second portion 220 may be integrally formed with, attached with an adhesive, and/or coupled to or otherwise attached to the pin 202.

The second portion 220 preferably includes a lower surface 230, which is configured to mate with the top surface 26 of the implant 10. As with the healing abutment 150, the lower surface 230 is preferably configured such that, when the impression coping 200 is secured to the implant 10 a smooth transition is formed between the outer surfaces of the implant 10 and the outer surfaces of the second portion 220. The top surface 232 of the second portion may be configured to abut against the lower surface of the upper portion 206 of the pin 202. In the illustrated embodiment, the second portion 220 has a generally cylindrical shape. However, in modified portions, the shape of the second portion 220 may be non-cylindrical (e.g., conical).

The first and second portions may be made of any of a variety of materials. In one embodiment, the first portion is made from titanium and the second portion is made from rubber or a rubber like material, such as, for example, a thermoplastic elastomer (e.g., Santoprene®).

Figure 8:
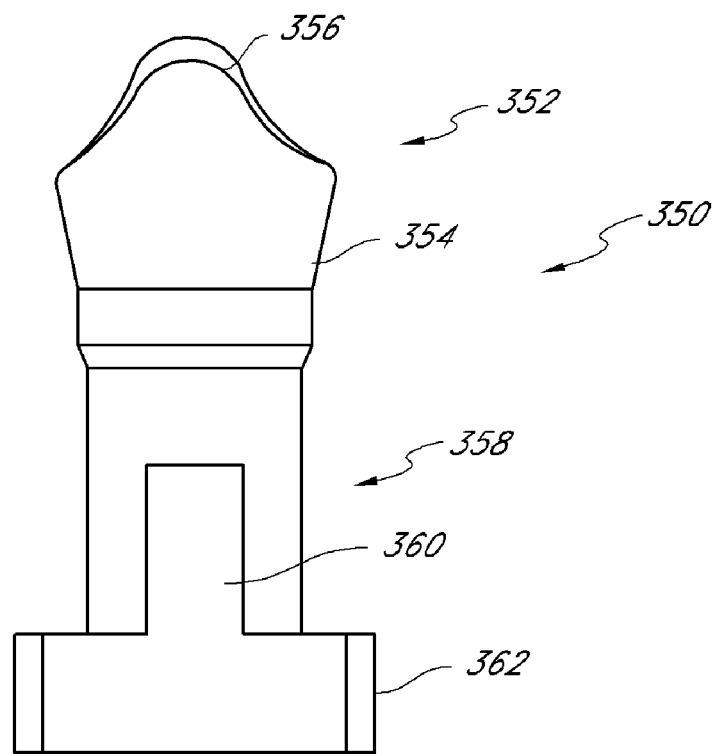
FIG. 8 is a side view of an exemplary embodiment of an analogue of a dental implant having certain features and advantages according to the present invention.

The impression pin 200 may be used in any of a variety of known or conventional techniques to reproduce in a stone or plaster analogue of the patient's mouth the axial orientation and position of the dental implant 10. In one embodiment of use, the post of the impression pin 200 is inserted into the implant and the lower surface of the second portion lies adjacent or close to the upper surface of the implant. An impression of the patient's mouth is then taken using close tray techniques. The impression is then removed from the mouth leaving an impression of the upper portion 202 of the impression pin 200. The impression pin 200 then may be removed from the implant 10 and the upper portion 202 may be repositioned in the impression. Before or after the impression pin 200 is repositioned in the impression, the impression pin 200 may be inserted into an analogue 300 (see FIG. 8) of the dental implant 10. As shown in FIG. 8, the analogue may having an upper portion 352, which includes a collar 354, a top surface 356 and bore (not shown) that generally corresponds to the shape and configuration of the collar 16, the top surface 26 the and bore 40 of the implant 10. The dental restoration also includes a lower portion 358, which may include one or more flat sides 360 or other anti-rotational features and a lower flange 362 or other retention enhancing features (e.g. grooves) configured for being embedded in stone or plaster material.

With the analogue attached to the impression pin, stone or plaster material may be poured into the impression to form stone or plaster analogue of the patient's mouth. The stone or plaster analogue may then be used to form the final restoration 400, described in more detail below) using conventional techniques that may involve using a coping and/or modifying the abutment on the stone model (see e.g., co-pending U.S. patent application Ser. No. 09/881,860, filed Jun. 15, 2001, entitled "COPINGS WITH STANDOFFS", which is hereby incorporated by reference herein). In other embodiments, various commercially available productions CAD/CAM systems may also be used to scan the stone or plastic model and to guide the design and creation of the final restoration (e.g., the system marketed and used by Nobel Biocare under the trademark Procerar™) (see also e.g., U.S. Pat. Nos. 6,062,861, 5,938,446, 5,880,962, 5,752,828, 5,733,126, 5,652,709, 5,587,912, 5,440,496, which are hereby incorporated by reference in their entirety herein). In other embodiments, prefabricated copings and/or final restorations may also be used.

Figure 9A:
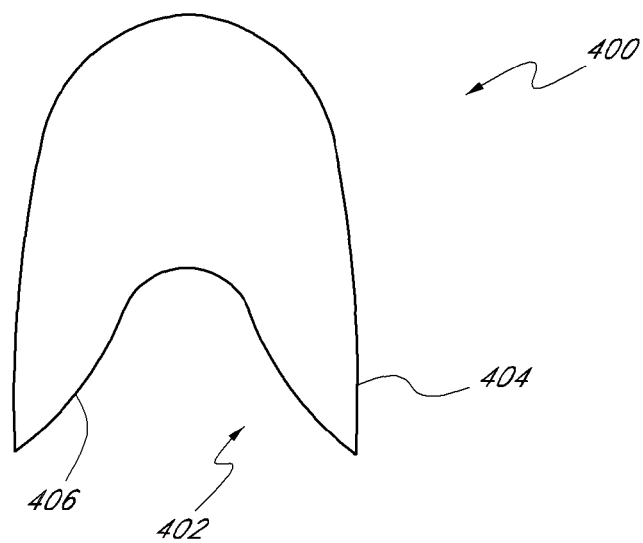
FIG. 9A is a side view of a final restoration configured to mate with the implant of FIG. 1A.
Figure 9B:
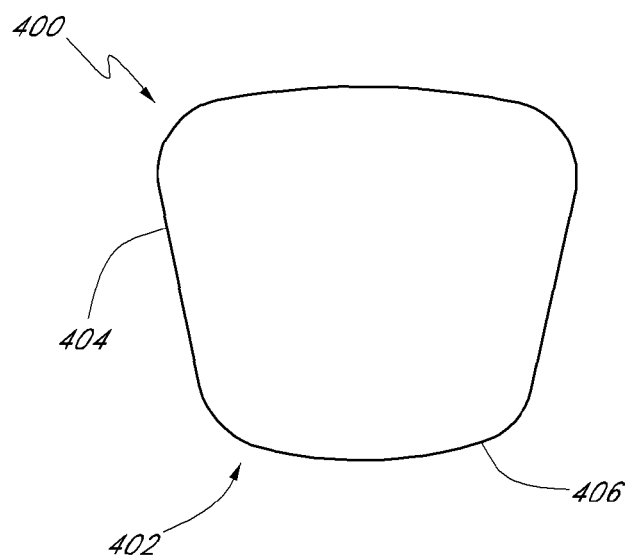
FIG. 9B is a front view of the final restoration of FIG. 9A.

FIGS. 9A-B illustrates the final restoration 400, which can be used with the implant 10 and abutment 52 described above. The final restoration 400 includes an inner surface (not shown), which is configured to fit over the upper portion 64 of the abutment 52. The final restoration 400 preferably also includes a lower surface 402, which is configured to mate with the top surface 26 of the implant 10. In one embodiment, the lower surface 402 is configured such that the final restoration 400 is secured on top of the abutment 52 and the implant 100, the side wall 24 of the implant 10 and an outer surface 404 of the final restoration 400 form a generally smooth transition. For example, the dimensions and contours of the outer edge 28 of the top surface 26 may closely match the dimensions and contours of an outer edge 406 of the lower surface 402 of the final restoration 400. In another embodiment, the final restoration 400 may be configured such that the outer edge 506 of the final restoration 400 lies partially or wholly within and/or beyond the outer edge 28 of the top surface 26 of the implant 10. For example, in one arrangement, the outer edge 406 of the final restoration 400 lies within the outer edge 28 of the implant 10. In such an arrangement, a portion of the top surface 26 of the implant 10 is exposed and may form a "horizontal" tissue apposition surface.

In one embodiment, the final restoration 406 is secured to the abutment 52 using dental cement or other adhesives. In other embodiments, the final restoration 400 may be provided with a bore and may be coupled to the abutment, an intermediate member and/or the implant via a bolt (not shown) In still other embodiments, the final restoration may be secured to one or more intermediate members (not shown), which are in turn coupled to the abutment by, for example, using cement or other adhesives or a screw. The final restoration 400 may made of a variety of materials traditionally used in the art, such as, for example, ceramics, porcelain etc. It should also be appreciated that the final restoration 406 may be used in combination with an O-ring as described above with reference to FIG. 5E.

The embodiments described above have several advantages. For example, the illustrated implant 10 has a bone apposition surface 20 that follows the naturally occurring contours of the a patient's bone-tissue morphology. This arrangement reduces alveolar bone loss. In a similar manner, the interface between the final restoration 400 and the dental implant 10 follows the naturally occurring contours of the patient's bone-tissue morphology. This arrangement encourages uniform tissue growth above the bone tissue and minimizes the amount of the dental implant 10 that extends above the bone-tissue. In contrast, in prior art implants, substantial portions of the dental implant extend above the soft-tissue, which can create undesirable "shadows" in the gum-tissue. In addition, the interaction between top surface 26 of the implant contacts the lower surface 402 of the final restoration 400, provides an additional anti-rotational structure between the final restoration 402 and the implant 10.

It should also be appreciated that implants and abutments described above may be used with temporary restoration that is configured to provide the patient with a temporary functional or esthetic benefits. In such an embodiment, the temporary restoration may be configured as described above and may be made from any suitable material, such as, for example, titanium or ceramic. In other embodiments, the abutment may be integrally formed with or permanently attached to the implant. Such a "one-piece" implant may be particularly useful for replacing smaller teeth.

FIGS. 10A and 10B illustrate an insertion tool 450 that may be used to insert the dental implants described above into a patient's jawbone. The insertion tool 450 includes a post 452 that is configured to fit within the post receiving chamber 44 of the implant. As mentioned above, the post receiving chamber 44 can include anti-rotational features 48. If the post receiving chamber 44 includes such anti-rotational features 48, the post 452 preferably includes corresponding structures so as to prevent the insertion tool 450 from rotating with respect to the implant body 10. In the illustrated embodiment, the post 452 includes two flat sides 454, which corresponds to two flat sides 48 in the post receiving chamber 44 so as to prevent relative rotation between the insertion tool 450 and the dental implant 10.

The insertion tool 450 includes a torque receiving member 454. The torque receiving member 456 is configured to transmit torque from a torque tool (e.g., a wrench) to the insertion tool 450. In this manner, the torque generated by the tool can be transmitted to the implant 10 through the insertion tool 450. In the illustrated embodiment, the torque receiving member 456 has a pentagonal cross-section. It should be appreciated that the torque receiving member 114 can be formed into a wide variety of other suitable shapes that may be used with efficacy, giving due consideration to the goals of providing anti-rotation between the torque tool and the insertion tool. For example, the torque receiving member 456 may comprise one or more radially inwardly or outwardly extending splines or recesses, flats, polygonal configurations and other anti-rotation complementary surface structures.

The illustrated insertion tool 454 preferably also includes a handpiece receiving portion 458 is sized and dimensioned to fit within a commercial handpiece drill. Typically, the handpiece receiving portion 458 will include a D-shaped key 460 as depicted in FIGS. 10A and 10B. Accordingly, the handpiece receiving portion 458 can be irrotatably locked within the handpiece so that torque can be transmitted from the handpiece to the insertion tool 450. Although a D-shaped key is used in the preferred embodiment, it should be understood that the key may be in the form other shapes as long as that, when in engaged with the handpiece, the key prevents the insertion tool 450 from rotating with respect to the handpiece and from falling out of the handpiece The insertion tool 450 includes a plurality of depth markers 462. In the illustrated embodiment, the depth markers 462 comprise annular grooves. In other embodiments, the depth markers 462 may be formed in a variety of other ways, such as, for example, laser etching, paint, protrusions, etc. The depth markers 462 may be used to guide the dental practitioner when inserting a dental implant into the patient's jawbone. For example, the depth makers 462 are preferably uniformly spaced and arranged so as to indicate the distance from the top of the implant to the top of the gum tissue. In this manner, the thickness of the gum tissue can be determined without requiring incisions to be made around the adjoining/adjacent tissue so as to raise a tissue flap for depth reference. Instead, a probe may be used along the insertion tool 450 to determine the position of the alveolar crest. In such an arrangement, the thickness of the gum tissue may be determined by reference to the depth markers 462 and the implant 10 can be appropriately positioned with respect to the alveolar crest and the top of the gum tissue.

The post 452 preferably includes a releasable retention feature 464, which is configured to releaseably engage the central bore 40 of the dental implant 10. The post 452 may include a variety of releasable retention features, such as, for example, prongs or compressible material, for creating a releasable retention force between the dental implant 10 and the insertion tool 450. In the illustrated embodiment, the releasable retention feature 464 comprises a resilient O-ring 465 (shown in cross-section in FIGS. 10A and 10B) positioned within an annular ridge and recess 466. The O-ring 465 is configured to engage the inner surfaces of the central bore 40 in a friction and/or interference fit. In this manner, the dental practitioner may temporarily attached the insertion tool 450 to the implant 10 so as to remove the implant from a package or container.

FIGS. 11A-12D illustrate an exemplary embodiment of an centering post 500 (FIGS. 11A-11D) and an abutment 502 (FIGS. 12A-C) that may be used with the implant 10 described above. With initial reference to FIGS. 11A-11D, the centering post 500 includes a lower post 504, which is configured to fit within the post receiving section 44 of the implant 10, and an upper portion 506, which is configure to fit, at least partially, within the enlarged diameter portion 50 of the post-receiving section 44. In the exemplary embodiment, the upper portion 506 includes a pair of flat sides 508 that correspond to the pair of flat sides 48 in the enlarged diameter portion 50 of the implant 10. Of course, in modified embodiments, the centering post 500 may not include anti-rotational features or may include anti-rotational features of different forms (e.g., more or less flat sides, grooves, protrusions etc.) depending upon the configuration of the implant 10.

The upper portion 506 defines a scalloped shoulder 510. The shoulder 510 has an outer edge 512 that generally follows the contours of the inner edge of the top surface 26 of the implant 10. The shoulder 510 also includes an inner edge 514 that generally follows the contours of the inner edge of the top surface 26 of the implant 10. A generally cylindrical extension 516 lies within and extends above the inner edge 514 of the shoulder 510. In the illustrated embodiment, the extension 516 is generally cylindrical in shape; although in modified embodiments the extension 516 may have other shapes (e.g., conical, rectangular etc.).

Figures 14A, 14B:
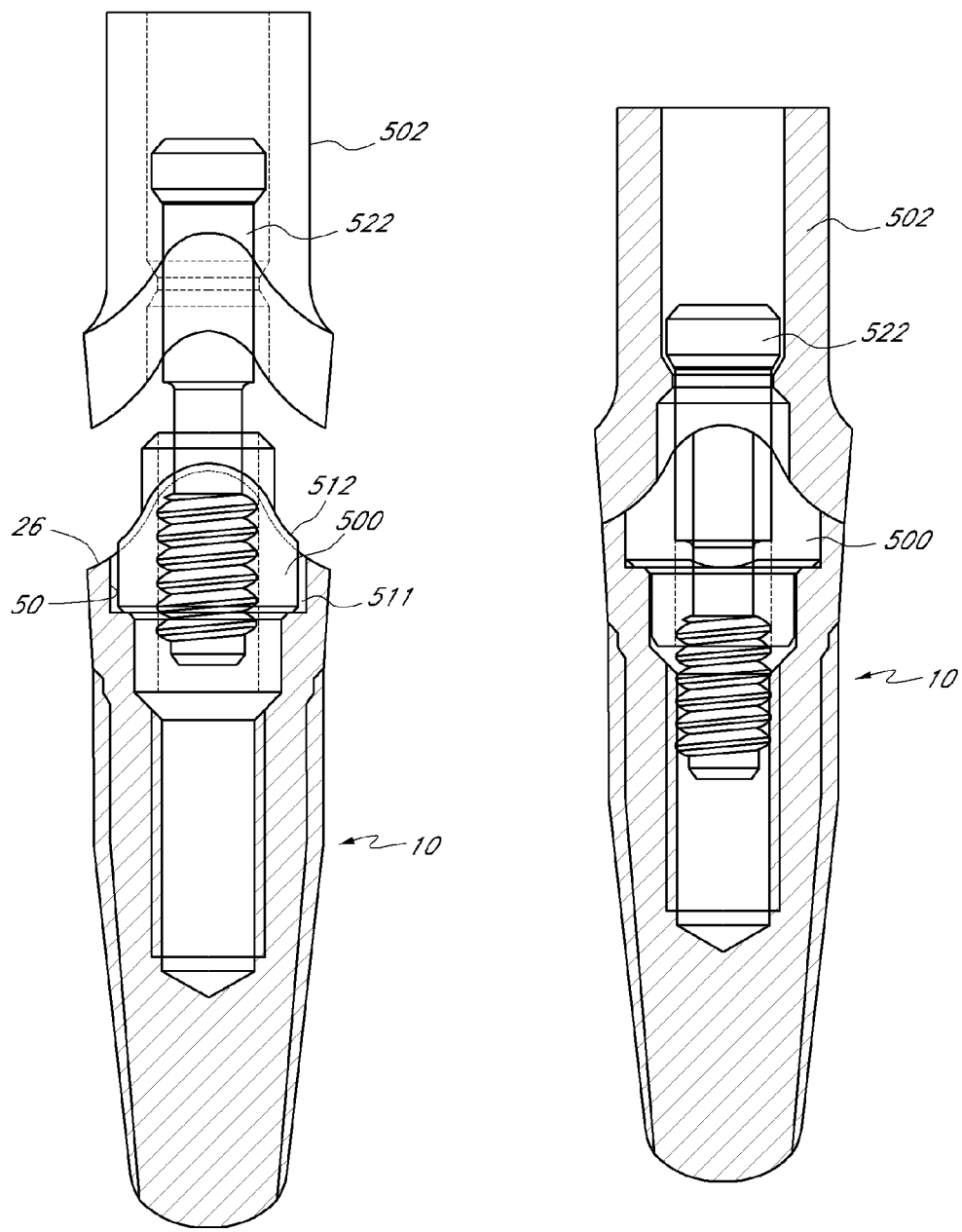
FIG. 14A is a partial cross-sectional view of the coupling screw, the abutment, the centering post and the dental implant of FIG. 13A.
FIG. 14B is a partial cross-sectional view of the coupling screw, the abutment, the centering post and the dental implant of FIG. 13A assembled together.

With continued reference to FIGS. 11A-D, the centering post 500 includes central bore 520 for receiving a portion of a coupling screw 522. As seen in FIG. 14A, in the exemplary embodiment, centering post 500 is configured such that when initially positioned in the implant 10, the outer edge 512 of the shoulder 510 lies slightly above the inner edge of the top surface 26 of the implant 10. In one embodiment, the shoulder 510 lies approximately 0.1 to. 0.5 millimeters above the top surface 26 of the implant 10. In addition, the upper portion 506 is preferably configured such that a small gap 511 exists between the outer surface of the centering post 500 and the enlarged diameter portion 50 of the implant 10. In one embodiment, the small gap 511 is approximately 0.005 to 0.1 millimeters wide.

The centering post 500 is advantageously made from an elastic material. In one embodiment, the centering post 500 is made from rubber or a rubber like material, such as, for example, a thermoplastic elastomer (e.g., Santoprene®). In other embodiments, only portions of the centering post 500 are made with or covered by an elastic material. For example, in one embodiment, one or more portions of the centering post 500 that contact the implant 10 and/or the abutment 502 are made from or covered by the elastic material. In one such embodiment, the upper portion 506 may be made from elastic material and the lower post 504 and/or the extension 516 may be made from a non-elastic material (e.g., a metal or plastic material).

Turning now to FIGS. 12A-D, the abutment 502 will now be described. The abutment 502 generally comprises a lower portion 530, an upper portion 532 and a central bore 534 that extends through the abutment 502. The lower portion 530 defines an lower surface 536, which has a scalloped shaped configured to mate with the top surface 26 and of the implant 10 and the shoulder 510 of the centering post 500. In one embodiment, the lower surface 536 includes an outer edge 538, which generally follows the shape of the outer edge of the top surface 26 of the implant 10 such that a generally smooth transition is formed between the collar of the implant 10 and the abutment 502. In another embodiment, the abutment 502 may be configured such that the outer edge 538 of the abutment 502 lies partially or wholly within and/or beyond the outer edge 28 of the top surface 26 of the implant 10. For example, in one arrangement, the outer edge 538 of the abutment 502 lies within the outer edge 28 of the implant 10. In such an arrangement, a portion of the top surface 26 of the implant 10 is exposed and may form a "horizontal" tissue apposition surface. It should also be appreciated that the abutment 502 may be used in combination with an O-ring as described above with reference to FIG. 5E.

The lower surface 538 also includes and inner edge 540, which generally follows the inner edge 514 of the centering post 500. The lower portion 530 also includes a side wall 542, which in the illustrated embodiment tapers slightly in the direction of the upper portion 532. However, in modified embodiments, the side wall 542 may be cylindrical or another modified shape.

Figure 12E:
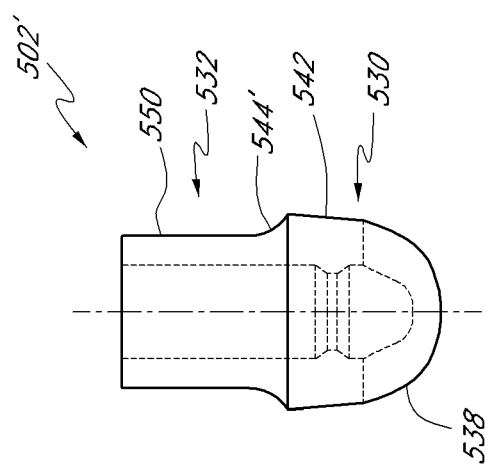
FIG. 12E is a side view of a modified abutment.
Figure 12F:
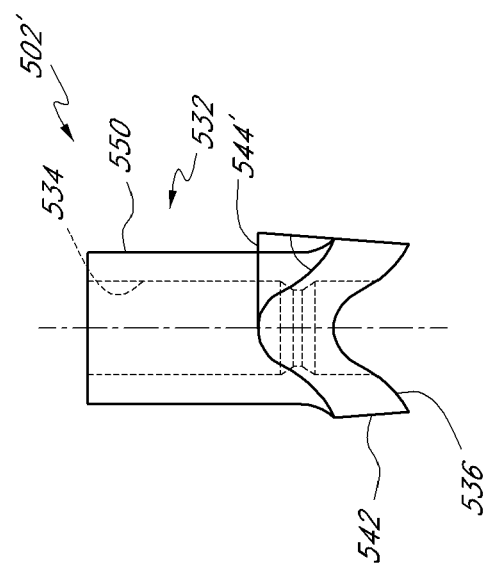
FIG. 12F is a rear view of the modified abutment of FIG. 12E.

The upper portion 532 includes a shoulder 544 (see also FIG. 13C), which preferably generally follows the contours of the top surface 26 of the implant 10. As such, the shoulder 544 includes an outer edge 546, which generally follows the shape of the outer edge of the top surface 26 of the implant 10. The shoulder 544 also includes and inner edge 548 (see FIG. 13C), which follows the contours of the outer edge 546. A generally cylindrical post 550 lies within and extends above the inner edge 548 of the shoulder 544. The shoulder 544 and the post 550 are configured to support a final restoration, which may be formed in a manner as described above. In modified embodiments, the post 550 may be formed in a variety of other shapes for supporting the final restoration. For example, the post 550 may be angled as described above with reference to FIG. 2E. In still other embodiments, the shoulder 544 of the abutment may be modified. For example, FIGS. 12E and 12F illustrate a modified abutment 502' in which the shoulder 544' has a generally flat side that may be positioned on the rear or lingual side of the implant 10. Such an arrangement may reduce machining costs while still providing the front or facial side of the abutment 502 with a scalloped shape. It should also be appreciated that the final restoration 406 may be used in combination with an O-ring positioned between the abutment and the final restoration.

As seen in FIG. 12C, the central bore 534 extends through the abutment 502. The central bore 534 advantageously includes a narrowing portion 552 (see FIG. 12D) that includes a tapered shoulder 554, a cylindrical portion 556 and a tapered expansion portion 558. The narrowing portion 552 provides a seat for supporting the coupling screw 522 and in other embodiments may comprise a simple shelf and/or various combinations and sub-combinations of the tapered shoulder 554, the cylindrical 556 and the tapered expansion portions 558.

Figures 13A, 13B:
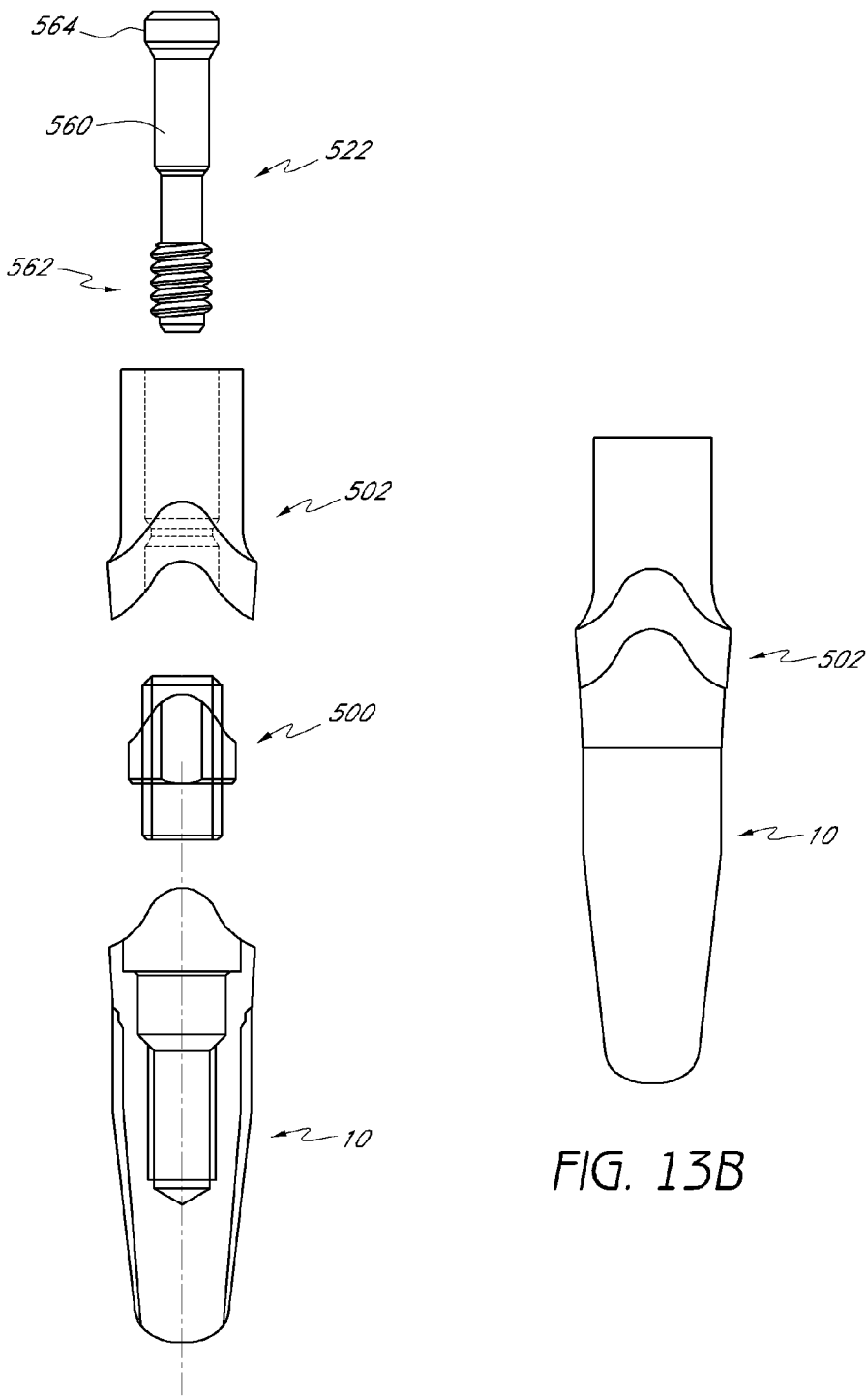
FIG. 13A is a side view of the centering post and abutment of FIGS. 11A and 12A with a coupling screw and the dental implant of FIG. 1A.
FIG. 13B is a side view of the abutment of FIG. 12 coupled to the dental implant of FIG. 12A.
Figure 13C:
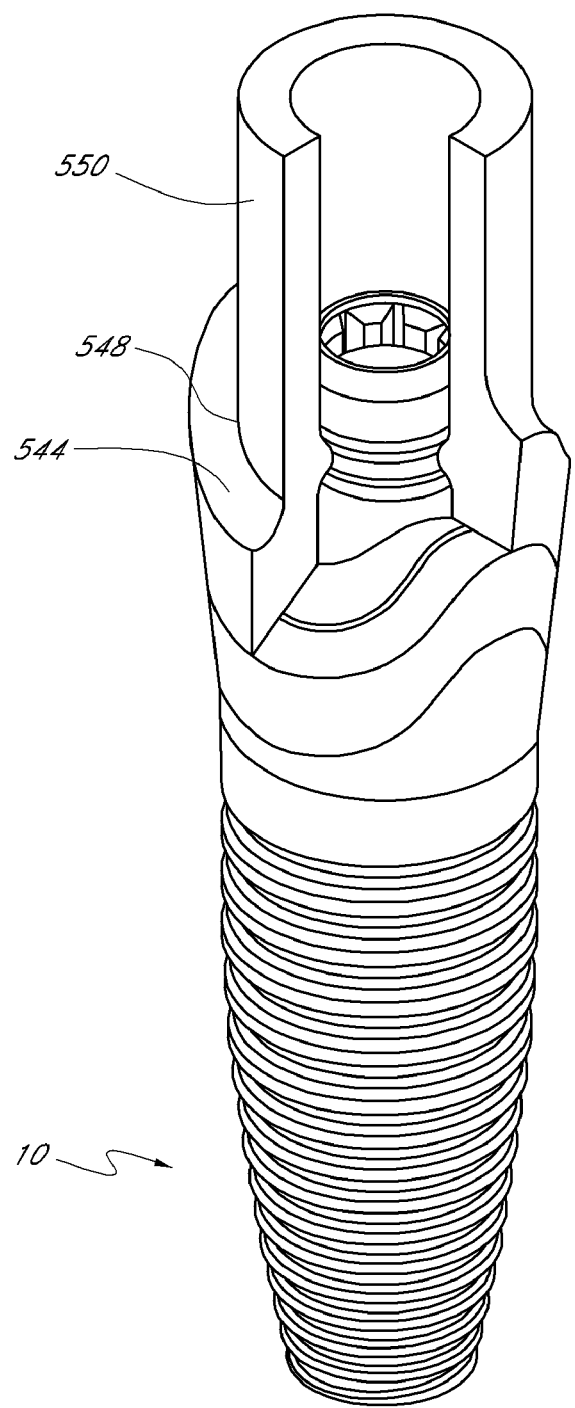
FIG. 13C is a side perspective view of the abutment and implant of FIG. 12B with a portion of the abutment removed to show the coupling screw.

As seen in FIG. 13A, the coupling screw 522 of the exemplary embodiment comprises an elongated shaft 560, which includes a threaded lower portion 532 and an enlarged diameter head portion 564. As shown in FIG. 13C, the enlarged head portion 564 may include any of a variety of rotational engagement connections, such as, for example, a tapered recess comprising plurality of concave side portions interconnected by flat or slightly curved side portions as described above.

In one embodiment of use, the centering post 500 is positioned within the central bore 40 of the implant 10. The abutment 502 is then fitted over the centering post 500 and onto the top surface 26 of the implant 10. The coupling screw 522 is used to secure the abutment to the implant 10 as the coupling screw 522 extends through the abutment 502 and the centering post 500 and the lower portion 562 engages the threaded chamber 42 of the implant 10. As the coupling screw 522 is tightened, the elastic centering post 500 is compressed in a vertical direction and expands in a horizontal direction to fill the enlarged diameter portion of the implant 10. See FIGS. 14A and 14B. In addition, the shoulder 510 of the centering post 500 forms a tight seal against the lower surface 536 of the abutment.

This arrangement is particularly advantageous when the abutment 502 is made of a ceramic material (e.g., aluminum oxide) or similar material. Such materials are typically more difficult to machine and form as compared to an abutment made of metal or plastic materials. Thus, it is more difficult to match the contours of the lower surface 536 to the contours of the top surface 26 of the implant 10. As such, there may be small gaps between the top surface 26 of the implant 10 and the lower surface of the abutment 502. Such gaps may allow bacteria and tissue to enter the central bore 40 of the implant 10. However, the arrangement described above may significantly reduce or prevent bacteria from entering the bore as the centering post 500 forms a tight seal with the abutment 502 and/or the implant 10.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A dental implant assembly for supporting a dental prosthesis, the assembly comprising:
    a dental implant comprising a body portion located at a distal end of the dental implant, the body portion configured to lie at least substantially below a crest of a patient's jawbone, a collar portion located at a proximal end of the dental implant, the collar portion forming a mating surface which defines an outer edge that has at least one peak and valley to match the contours of a patient's soft tissue; a central bore that extends through the collar portion and into the implant body portion; the central bore including an engagement portion and a post portion;
    a post that includes an upper portion, a lower portion, a shoulder between and wider than the upper portion and the lower portion, and an inner bore extending through the post, the lower portion fitting at least partially within the post portion of the central bore of the implant, the post having at least one elastic portion;
    a ceramic abutment having a central bore and a lower mating surface that is configured to mate with the mating surface of the dental implant and an upper surface of the shoulder of the post, the upper portion of the post extending into the central bore of the ceramic abutment; and
    a coupling member extending through the central bore of the abutment and the inner bore of the post and configured to engage the engagement portion of the implant, wherein advancement of the coupling member advances the lower mating surface of the ceramic abutment toward the mating surface of the dental implant;
    wherein the dental implant assembly is configured to have a first configuration in which the lower mating surface of the ceramic abutment mates with the upper surface of the shoulder of the post, and wherein the dental implant assembly is configured to have a second configuration in which the coupling member has been advanced relative to the first configuration such that an interface between the lower mating surface of the ceramic abutment and the mating surface of the dental implant circumscribes the post.

2. The assembly as in claim 1, wherein the upper surface of the shoulder of the post follows the contours of the mating surface of the implant.

3. The assembly as in claim 2, wherein the at least one elastic portion of the post includes the shoulder and when the coupling member is tightened a seal is formed between the shoulder of the post and the lower mating surface of the abutment.

4. The assembly as in claim 2, wherein when the post is positioned in the central bore of the implant the shoulder lies above the mating surface of the implant.

5. The assembly as in claim 1, wherein the at least one elastic portion of the post includes the lower portion of the post and when the coupling member is tightened a seal is formed between the lower portion and the post portion.

6. The assembly as in claim 1, wherein the post is made of an elastic material.

7. The assembly as in claim 1, wherein the dental implant includes a bone apposition surface on the body portion that extends to the collar portion.

8. The assembly as in claim 7, wherein the bone apposition surface has an upper edge positioned on the collar portion, the upper edge having at least one peak and one valley to match the contours of a patient's soft tissue.

9. The assembly as in claim 8, wherein the surface of the collar portion between the upper edge and the outer edge is polished.

10. The assembly as in claim 9, wherein the surface of the collar portion between the upper edge and the outer edge has a tooth like color.

11. The assembly as in claim 1, wherein the mating surface of the implant is at least partially slanted with respect to a longitudinal axis of the implant.

12. An abutment and sealing post combination for supporting a dental prosthesis on a dental implant, the combination comprising:
    an abutment having a central bore, an upper portion and a lower portion, the lower portion forming a mating surface which defines an outer edge that has at least one peak and valley to match the contours of a patient's soft tissue, the mating surface configured to mate with a corresponding mating surface of the dental implant;
    an elastic post that includes an upper portion that includes an first portion that fits into the central bore of the abutment, a lower portion and an inner bore extending through the upper and lower portions, the lower portion being configured to fit within the dental implant, the upper portion further comprising a shoulder that follows the contours of the mating surface of the implant;
    wherein the abutment is configured to be advanced toward the implant, and wherein in a first position of the abutment relative to the implant the mating surface of the abutment mates with the shoulder of the elastic post, and wherein in a second position of the abutment relative to the implant the mating surface of the abutment mates with the shoulder of the elastic post and a corresponding mating surface of the dental implant such that an outer periphery of the shoulder lies entirely within the outer edge of the mating surface of the abutment.

13. A method for installing a dental prosthesis comprising:
    providing a dental implant comprising a body portion located at a distal end of the dental implant, the body portion configured to lie at least substantially below a crest of a patient's jawbone, a collar portion located at a proximal end of the dental implant, the collar portion forming a mating surface which defines an outer edge that has at least one peak and valley to match the contours of a patient's soft tissue; a central bore that extends through the collar portion and into the implant body portion, the central bore including a threaded portion and a post portion;

providing a post that includes an upper portion, a lower portion and an inner bore extending through the upper and lower portions, the lower portion being configured to fit at least partially within the post portion of the implant, the post having at least one elastic portion;

providing a ceramic abutment having a central bore and a lower mating surface that is configured to mate with the mating surface of the dental implant; and providing a coupling member that is configured to extend through the central bore of the abutment and the inner bore of the post and to engage the engagement portion of the implant;

inserting the dental implant into a bone;

inserting the post into the central bore of the implant, positioning the ceramic abutment over the post such that the lower mating surface of the ceramic abutment mates with a corresponding mating surface of the post; and coupling the ceramic abutment to the dental implant by tightening the coupling member and compressing the post to form a tight seal between the ceramic abutment and the implant and wherein the step of coupling the ceramic abutment to the implant comprises completely covering the post.

* * * * *